(12) United States Patent
Aoyagi

(10) Patent No.: US 12,743,760 B2
(45) Date of Patent: Sep. 22, 2026

(54) METHOD FOR DETECTING MICROORGANISMS

(71) Applicant: ASAHI SOFT DRINKS CO., LTD., Tokyo (JP)

(72) Inventor: Makoto Aoyagi, Moriya (JP)

(73) Assignee: ASAHI SOFT DRINKS CO., LTD., Tokyo (JP)

( * ) Notice: Subject to any disclaimer, the term of this patent is extended or adjusted under 35 U.S.C. 154(b) by 289 days.

(21) Appl. No.: 18/569,524

(22) PCT Filed: Dec. 6, 2021

(86) PCT No.: PCT/JP2021/044692
§ 371 (c)(1),
(2) Date: Dec. 12, 2023

(87) PCT Pub. No.: WO2022/264454
PCT Pub. Date: Dec. 22, 2022

(65) Prior Publication Data

US 2024/0281949 A1 Aug. 22, 2024

(30) Foreign Application Priority Data

Jun. 14, 2021 (JP) ................................ 2021-098715

(51) Int. Cl.

*G06T 7/00* (2017.01)
*C12M 1/34* (2006.01)
*C12Q 1/22* (2006.01)

(52) U.S. Cl.

CPC .............. *G06T 7/0002* (2013.01); *C12Q 1/22* (2013.01); *G06T 2207/10056* (2013.01);
(Continued)

(58) Field of Classification Search

CPC ......... G06T 7/0002; G06T 2207/10056; G06T 2207/10064; G06T 2207/20081;
(Continued)

(56) References Cited

U.S. PATENT DOCUMENTS

2008/0108553 A1* 5/2008 Luan ........................ C12Q 1/02
435/325
2017/0029864 A1* 2/2017 Straus ...................... C12Q 1/06
(Continued)

FOREIGN PATENT DOCUMENTS

EP 3806101 A1 4/2021
JP 2005-502354 A 1/2005
(Continued)

OTHER PUBLICATIONS

International Search Report for International Patent Application No. PCT/JP2021/044692 (Jan. 18, 2022).
(Continued)

*Primary Examiner* — Jennifer Mehmood
*Assistant Examiner* — Dustin Bilodeau
(74) *Attorney, Agent, or Firm* — Merchant & Gould P.C.

(57) ABSTRACT

The present invention provides a method for detecting microorganisms, comprising an imaging step in which a membrane filter that filters a liquid is attached to a surface of a plate medium and cultured for a predetermined period of time, followed by peeling from the plate medium and fluorescently staining to capture fluorescence images; a learning data generation step of inputting, for each of the plurality of the fluorescence images, microorganism position information indicating the microorganism positions on the fluorescence images to generate, as learning data, the fluorescence images and the microorganism position information; a step of generating a trained model by performing machine learning based on the learning data; and a step of
(Continued)

determining the presence or absence of microorganisms using the trained model for the fluorescence images input as an inspection target, and the like.

8 Claims, 10 Drawing Sheets

(52) U.S. Cl.
CPC ............... *G06T 2207/10064* (2013.01); *G06T 2207/20081* (2013.01); *G06T 2207/30024* (2013.01)

(58) Field of Classification Search
CPC .. G06T 2207/30024; C12Q 1/22; C12Q 1/02; C12Q 1/04; C12Q 1/06; C12M 1/00; C12M 1/34
USPC .......................................................... 382/128
See application file for complete search history.

(56) References Cited

U.S. PATENT DOCUMENTS

2019/0204292 A1 7/2019 Mimura
2020/0386684 A1 12/2020 Nomura et al.
2021/0062138 A1* 3/2021 Piao ........................ C12Q 1/02
2021/0090238 A1* 3/2021 Gallagher-Gruber ........................ G01N 15/1433
2021/0106231 A1 4/2021 Radhakrishnan et al.
2021/0260582 A1 8/2021 Ohno
2023/0071901 A1* 3/2023 Ikeda .................... G06T 7/0012
2023/0414669 A1* 12/2023 Nakamura ......... G01N 15/1433

FOREIGN PATENT DOCUMENTS

JP 2012-080802 A 4/2012
JP 5850205 B2 2/2016
JP 2016-174581 A 10/2016
JP 2019-012084 A 1/2019
JP 2019-208377 A 12/2019
JP 2020-054247 A 4/2020
JP 2020-123044 A 8/2020
JP 2021-002320 A 1/2021
WO 03/022999 A2 3/2003
WO 2017/221592 A1 12/2017
WO 2019/230302 A1 12/2019
WO 2020/021604 A1 1/2020

OTHER PUBLICATIONS

Decision of Rejection issued for Japanese Patent Application No. 2021-098715 (Jun. 14, 2022).

* cited by examiner

N1
N2
C11
C12
P1
C21
C22
P2
C31
C32
P3
U4
C41
C42
U5
C51
C52
U6
C61
C62
SM61
Convolution
Pooling
Upsampling
Softmax

METHOD FOR DETECTING MICROORGANISMS

This application is a National Stage Application of PCT/JP2021/044692, filed Dec. 6, 2021, which claims benefit of priority to Japanese Patent Application No. 2021-098715 filed on Jun. 14, 2021, and which applications are incorporated herein by reference. To the extent appropriate, a claim of priority is made to each of the above disclosed applications.

TECHNICAL FIELD

The present invention relates to a method for detecting microorganisms in a liquid such as a beverage, a learning device and a trained model used in the method, and an inspection device that performs the method.

BACKGROUND ART

Packaged beverages generally require sterilization to prevent deterioration in quality, particularly the propagation of bacteria, during distribution in the market. The sterilization process may be performed after filling the container, or a sterilized beverage may be aseptically filled into a sterilized container. Packaged beverages mass-produced in factories undergo a microorganism detection test to confirm that they have been properly sterilized prior to shipment. Packaged beverages in which microorganisms are detected by the inspection are deemed insufficiently sterilized and are not shipped, and only the packaged beverages in which no microorganisms are detected are shipped.

Microorganism detection tests for packaged beverages prior to shipment have traditionally been carried out by mixing and dispersing beverage samples with an agar medium in a petri dish, solidifying them on a plate medium, and culturing them, and then visually confirming the presence or absence of colonies. However, the culture method requires a culture time of 2 to 3 days until colonies large enough to be visually confirmed are formed. For this reason, it takes a long time to ship from the factory after production. Therefore, it is desired to further shorten the time required for the microorganism detection test.

As a method that shortens the time required for detection compared to the culture method, there is a fluorescence detection method in which a beverage sample is filtered and concentrated using a membrane filter, the filter used in the filtration is attached to a plate medium and cultured, and the resulting microcolonies are fluorescently stained to perform fluorescence observation. By fluorescently staining the microorganisms, it is possible to detect the microorganisms with a higher sensitivity than by visual inspection, and thus the culture time can be shortened. A fluorescence image of the fluorescently stained membrane filter is imaged using a fluorescence imaging device that combines a high-performance camera, light source, and fluorescence filter, and the resulting fluorescence image is analyzed to identify microorganisms on the membrane filter.

Although microorganisms can be detected quickly and with high sensitivity using the fluorescence detection method described above, beverages may contain impurities that emit autofluorescence, and contaminants other than microorganisms in beverages may also be fluorescently stained. In particular, in the case of beverages containing a large amount of milk components or fruit juices that can cause autofluorescence, for the acquired fluorescence image, it may be difficult to clearly distinguish between the bright spots derived from various impurities such as protein and fiber and the bright spots derived from microorganisms in the beverage sample, and the accuracy of microorganism detection is a problem. As a method to solve this problem, a technique is known that focuses on the difference in time change in the fluorescence reactions between microorganisms and impurities, and uses a rule-based image-processing software to perform differential processing of fluorescence images at the early and late stages of staining (Patent Document 1).

Recently, methods have also been developed that combine image analysis and deep learning image-processing software to detect objects from images. For the microorganism detection, there are known technologies or similar technologies that detect microbial colonies from culture media images using an algorithm generated by acquiring culture medium image data of a culture medium in which microorganisms are cultured and performing deep learning on the learning data including the culture medium type. For example, Patent Document 2 discloses a method of acquiring image data of a medium in which microorganisms are cultured and detecting microorganisms based on image data learned in advance. Moreover, Patent Document 3 discloses a method of acquiring image data of a medium in which microorganisms are cultured and calculating the number of microorganism colonies based on image data learned in advance. Patent Document 4 discloses a technique that can improve colony detection sensitivity by eliminating the influence of sample-derived colors from color feature values of pixels that constitute an image of a microbial colony. Patent Document 5 discloses an information-processing device that is capable of classifying Gram-stained bacteria based on data on which a person has previously determined the classification.

CITATION LIST

Patent Document

[Patent Document 1] Japanese Unexamined Patent Application, First Publication No. 2016-174581

[Patent Document 2] Japanese Unexamined Patent Application, First Publication No. 2020-54247

[Patent Document 3] Japanese Unexamined Patent Application, First Publication No. 2019-208377

[Patent Document 4] Japanese Patent No. 5850205

[Patent Document 5] Japanese Unexamined Patent Application, First Publication No. 2020-123044

SUMMARY OF INVENTION

Technical Problem

When a rule-based image-processing software is used, microorganisms and components other than microorganisms in a fluorescence image are distinguished based on the difference in change in fluorescence intensity with staining time. If the amount of change in fluorescence intensity with staining time differs greatly between microorganisms and other components, microorganisms and other components can be distinguished with high accuracy, and highly reliable microorganism detection results can be obtained. On the other hand, for microorganisms whose fluorescence intensity changes with staining time to the same extent as components other than microorganisms, it is difficult to distinguish between the microorganisms and other components, and false positives occur frequently. Among microorganisms, molds in particular are difficult to accurately detect from fluorescence images because the shapes of grown colonies are complex and there are large differences between bacterial species. Therefore, measures are needed to selectively detect only microbial colonies by improving the ability to distinguish between microbial colonies and other components.

Further, the microorganism detection methods described in Patent Documents 2 to 5 are based on detection using visible light. Therefore, no consideration is given to the fluorescent staining method or the influence of components other than microorganisms that occur in the fluorescent staining method.

An objective of the present invention is to provide a method for detecting microorganisms with high sensitivity and accuracy by distinguishing between microorganisms and other components in the acquired fluorescence images in a method for detecting microorganisms in a liquid using a fluorescence detection method, a learning device used in the method, and the like.

Solution to Problem

The present inventors have found that the ability to distinguish between the bright spots derived from microorganisms and the bright spots derived from components other than microorganisms can be improved and also the detection accuracy of microorganisms can be improved by analyzing fluorescence images using deep learning image-processing software and using an algorithm generated by deep learning of the difference in feature values between fluorescently stained microcolonies derived from microorganisms and components other than microorganisms in a method for detecting microorganisms in a liquid using a fluorescence detection method, thereby completing the present invention.

The methods for detecting microorganisms according to the present invention are the following [1] to [9].

[1] A method for detecting microorganisms in a liquid, comprising:

- a filtering step of filtering a liquid with a membrane filter;
- a culturing step of attaching the membrane filter after the filtering step to a surface of a plate medium and culturing for a predetermined period of time;
- a fluorescent staining step of fluorescently staining microorganisms on the membrane filter peeled off from the plate medium after the culturing step;
- an imaging step of imaging fluorescence images of the membrane filter after the fluorescent staining step;
- a learning data generation step of inputting, for each of the plurality of the fluorescence images, microorganism position information indicating the microorganism positions on the fluorescence images to generate, as learning data, the fluorescence images and the microorganism position information;
- a learning step of generating a trained model by performing machine learning based on the learning data; and
- an inspection step of determining the presence or absence of microorganisms using the trained model for the fluorescence images input as an inspection target.

[2] The method for detecting microorganisms according to [1], further comprising a pre-step of removing an edge portion of the membrane filter from the fluorescence images, wherein

- in the learning step, machine learning is performed based on the fluorescence images from which the edge portion of the membrane filter has been removed and the microorganism position information.

[3] The method for detecting microorganisms according to [1] or [2], wherein

- in the imaging step, the fluorescence images are imaged by irradiating excitation light of a fluorescent staining agent used for the fluorescence staining.

[4] The method for detecting microorganisms according to any one of [1] to [3], wherein

- the plate medium contains glucose, peptone and potato extract, and
- the peptone concentration is 2 to 5 g/L.

[5] The method for detecting microorganisms according to any one of [1] to [4], wherein the plate medium consists only of glucose, peptone, potato extract, and agar.

[6] The method for detecting microorganisms according to any one of [1] to [5], wherein the liquid is a beverage.

[7] A learning device comprising a learning unit configured to

- read, as learning data, fluorescence images obtained by imaging a membrane filter cultured with microorganisms collected from a liquid and fluorescently stained with a fluorescent staining agent for microorganisms and microorganism position information indicating the microorganism positions on the fluorescence images, and
- generate a trained model by performing machine learning based on the learning data.

[8] An inspection device comprising an inspection unit configured to determine the presence or absence of microorganisms in fluorescence images input as an inspection target using a trained model generated by performing machine learning based on fluorescence images obtained by imaging a membrane filter cultured with microorganisms collected from a liquid and fluorescently stained with a fluorescent staining agent for microorganisms and microorganism position information indicating the microorganism positions on the fluorescence images.

[9] A trained model for detecting microorganisms in a liquid, which

- is generated by performing machine learning based on fluorescence images obtained by imaging a membrane filter cultured with microorganisms collected from a liquid and fluorescently stained with a fluorescent staining agent for microorganisms and microorganism position information indicating the microorganism positions on the fluorescence images, and
- allows a computer to function to determine the presence or absence of the microorganisms in the fluorescence image input as the inspection object.

Advantageous Effects of Invention

According to the present invention, microorganisms in a liquid containing various components can be detected rapidly and with high sensitivity.

BRIEF DESCRIPTION OF DRAWING

FIG. 11(A) shows the measurement result of the number of colonies (learning amount) of the heat-resistant molds used for learning, and FIG. 11(B) shows the measurement result of the recovery rate (%).

DESCRIPTION OF EMBODIMENTS

Figure 1:
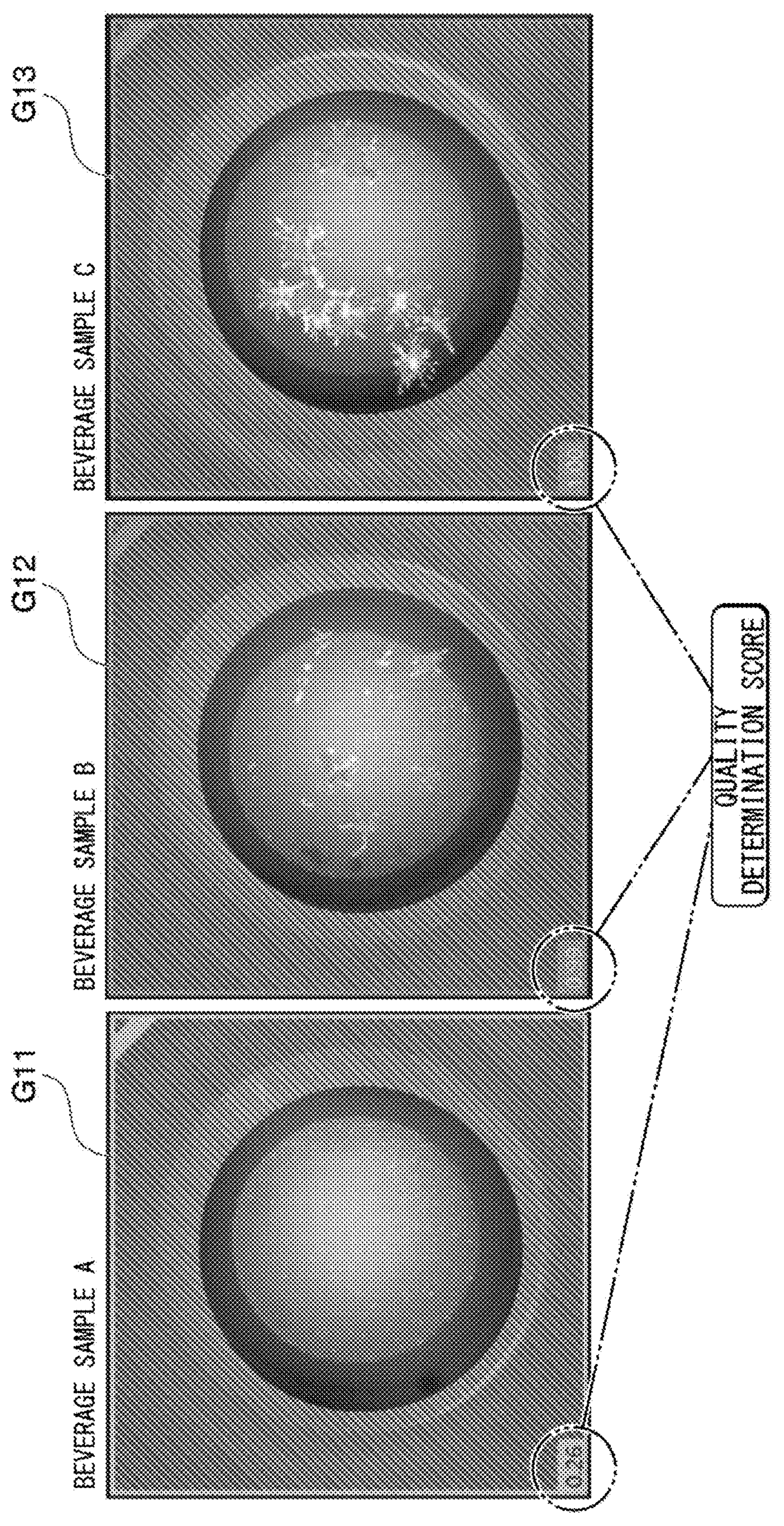
FIG. 1 is a schematic diagram showing a display example of inspection results according to an embodiment of the present disclosure.

The method for detecting microorganisms according to an embodiment of the present disclosure detects microorganisms in a liquid. The liquid as a test sample for detecting microorganisms (liquid test sample) is not particularly limited. Examples of the liquid include liquid foods, beverages, pharmaceuticals, cosmetics, and liquid compositions as the raw materials thereof, with beverages being particularly preferable.

Those beverages may be a beverage containing microorganisms such as lactic acid bacteria, yeast or the like, and may also be a beverage containing a component that emits autofluorescence such as an amino acid, protein, dietary fiber or the like. Furthermore, it may also be a non-alcoholic beverage such as a soft drink, a milky beverage or the like, or an alcoholic beverage. Examples of the soft drink include carbonated drinks such as ramune, soda pop, cola, ginger ale or the like; fruit and vegetable drinks such as concentrated fruit juices, fruit juice-containing drinks, fruit juices, vegetable juices, mixed fruit and vegetable juices, beverages containing pulp and vegetable pieces or the like; luxury drinks such as coffee drinks, black tea drinks, green tea drinks, oolong tea drinks, barley tea drinks, jasmine tea drinks, herbal drinks, cocoa drinks or the like; milky drinks containing milk components such as lactic acid bacteria beverages, fermented milk, milk, milk coffee drinks or the like; soy milk drinks; sports drinks; mineral water; non-alcoholic beverages with alcohol flavor such as non-alcoholic beer, non-alcoholic plum wine, non-alcoholic cocktails or the like; and the like. Examples of the alcoholic beverages include beer, wine, sake, shochu, whiskey, brandy, liqueurs, cocktails and the like.

The method for detecting microorganisms according to the embodiment of the present disclosure has high microorganism detection accuracy even for a liquid containing a substance that emits autofluorescence or a substance that can be fluorescently stained. For this reason, the liquid test sample is preferably a beverage containing a relatively large amount of a substance that emits autofluorescence or a substance that can be fluorescently stained. Specifically, beverages containing milk components, fruits, vegetables etc., such as milky beverages and fruit/vegetable beverages, are preferable.

In the method for detecting microorganisms according to the embodiment of the present disclosure, microorganisms to be detected are living microorganisms unintentionally contained in a liquid. For example, in the case of industrial products such as beverages, if microorganisms that are unintentionally contained in the liquid during the manufacturing process are not killed by sterilization, etc. and are still alive, there is a high possibility that the quality of the beverage product will be impaired during the distribution process, and there is also a risk to health if it is ingested by consumers. Therefore, hereinafter, microorganisms that are unintentionally contained in liquids such as beverages in a living state may be referred to as "harmful microorganisms". Specific examples of the harmful microorganisms include filamentous fungi (molds), yeasts, bacteria and the like.

In the method for detecting microorganisms according to the embodiment of the present disclosure, harmful microorganisms in a liquid are collected on a membrane filter and proliferated on the membrane filter to form colonies. The formed colonies are detected using fluorescent staining. Generally, 2 to 3 days of culture are required to form colonies large enough to be visible to humans. However, in the present invention, since even very small colonies (microcolonies) can be detected by using fluorescence, the culture time can be shortened and the harmful microorganisms can be detected more quickly.

When the liquid test sample is filtered through a membrane filter, various components in the liquid test sample are collected on the membrane filter along with harmful microorganisms. When a component that emits autofluorescence or a component other than the harmful microorganisms that can be fluorescently stained in the same way as the harmful microorganisms is collected on the membrane filter, fluorescence signals (bright spots) derived from the harmful microorganisms and fluorescence signals derived from the substances other than the harmful microorganisms exist in the fluorescence-stained image of the membrane filter. The fluorescence signals derived from the substances other than the harmful microorganisms are referred to as "noise", and the component derived from the liquid test sample that causes noise is referred to as "noise component".

Examples of the noise component include components that emit autofluorescence and components that can be fluorescently stained in the same way as the harmful microorganisms. Examples of the autofluorescent component include amino acids, peptides, dietary fibers, vitamin B2 (riboflavin), and the like. In addition, examples of the component that can be fluorescently stained in the same way as the harmful microorganisms include microorganisms such as lactic acid bacteria or yeast that were blended as raw materials and were killed by the final sterilization of the liquid test sample, components containing cells of shredded fruits or vegetables, and the like.

Specifically, the method for detecting microorganisms according to the embodiment of the present disclosure is a method for detecting microorganisms in a liquid, and includes the following steps:

- a filtering step of filtering a liquid with a membrane filter;
- a culturing step of attaching the membrane filter after the filtering step to a surface of a plate medium and culturing for a predetermined period of time;
- a fluorescent staining step of fluorescently staining the microorganisms on the membrane filter peeled off from the plate medium, after the culturing step;
- an imaging step of imaging fluorescence images of the membrane filter after the fluorescent staining step;
- a learning data generation step of inputting, for each of the plurality of the fluorescence images, microorganism position information indicating the microorganism positions on the fluorescence image to generate, as learning data, the fluorescence images and the microorganism position information;
- a learning step of generating a trained model by performing machine learning based on the learning data; and
- an inspection step of determining the presence or absence of the microorganism using the trained model for the fluorescence images input as an inspection target.

[Filtering Step]

In the filtering step, a liquid as a test sample for detecting microorganisms (liquid test sample) is filtered through a membrane filter. Specifically, the liquid test sample is poured into a funnel with a membrane on the bottom from the upper opening of the funnel and filtered. By suction-filtrating the beverage from the bottom of the funnel, a sufficient amount of harmful microorganisms in the liquid test sample can be collected on the membrane in a short period of time. Suction-filtration can be performed in the same manner as a general membrane filter method.

The membrane to be used is not particularly limited as long as it is a water-insoluble porous membrane having a size that allows the liquid components to pass through but not microorganisms. For example, a membrane filter with a pore size of 0.1 to 1.0 μm, preferably 0.15 to 0.9 μm, more preferably 0.45 to 0.8 μm can be used. Examples of the materials for the membrane filter include a nitrocellulose film, a mixed ester film of cellulose acetate and nitrocellulose, a polycarbonate film and the like.

In order to improve the detection accuracy of harmful microorganisms, it is preferable to prepare a plurality of types of membrane filters that collect microorganisms in the liquid test sample for each type of the liquid test sample. For the detection of microorganisms, 2 or more, preferably 5 or more, more preferably 10 or more membrane filters that collect microorganisms in the liquid test sample are prepared for each type of the liquid test sample.

The membrane filter that collects microorganisms in a liquid test sample is used not only to detect microorganisms in the liquid test sample, but also to generate learning data for generating a trained model. In order to generate learning data for generating a trained model, it is preferable to prepare a plurality of types of membrane filters that collect microorganisms in the liquid test sample for each type of liquid test sample. For example, in order to prepare learning data, 5 or more, preferably 10 or more, more preferably 15 or more membrane filters that collect microorganisms are prepared for each type of liquid test sample.

[Culturing Step]

In the culturing step, the membrane filter that has collected the microorganisms in the liquid in the filtering step is attached to a surface of a plate medium and cultured for a predetermined period of time. The plate medium to be used is not particularly limited as long as it contains a carbon source and a nitrogen source necessary for growth of molds, yeast, bacteria and the like. Glucose is preferable as the carbon source, and peptone, yeast extract, plant extract, and the like are preferable as the nitrogen source, since they can be assimilated by a wide variety of microorganisms. The peptone is not particularly limited, but casein peptone and meat peptone are preferable since they are widely used in microbial culture. Examples of the plant extracts include potato extract, malt extract, fruit juice, vegetable juice and the like. As the plant extract contained in the plate medium, potato extract is preferable since it contains trace metals and minerals such as copper and zinc that are necessary for the growth of fungi such as molds and yeast and is commonly used as a component of fungal culture media.

After culturing, the plate medium adheres to the membrane filter that is peeled off from the plate medium. That is, the autofluorescence component derived from the plate medium becomes a noise component. For this reason, the plate medium used in the culturing step is preferably a medium whose composition has been adjusted so as to suppress autofluorescence and enhance the growth of the microorganisms. Amino acids and peptides that are suitable as nitrogen sources are autofluorescent components, and therefore, if the amounts thereof are too large, there is a risk that noise may increase and the detection accuracy of microorganisms may decrease. On the other hand, nitrogen sources are important for promoting the growth of microorganisms. Therefore, the amount of amino acids and peptides in the plate medium used in the culturing step is preferably adjusted so as to balance the reduction of noise and the promotion of microorganism growth.

The plate medium used in the culturing step is preferably a medium consisting only of glucose, peptone, potato extract and agar. The plate medium containing glucose, peptone and potato extract can be obtained by mixing a Potato Dextrose Agar medium (PDA agar medium) (potato extract: 4.0 g/L, glucose: 20.0 g/L, agar: 15.0 g/L) and a Sabouraud glucose liquid medium (casein/meat peptone: 10.0 g/L, glucose: 20.0 g/L). Both PDA medium and Sabouraud glucose liquid medium are widely used for culturing filamentous fungi and yeasts.

As the plate medium in the culturing step, in particular, a medium prepared by adding agar to a medium containing a PDA medium and a Sabouraud glucose liquid medium with a peptone concentration within a range that achieves both noise-reduction and microbial growth-promotion, preferably 2 to 5 g/L, is used. Among these, a plate culture medium in which a Sabouraud glucose liquid medium is blended with a PDA medium in an amount of 20 to 30% by mass of the standard blending amount is preferable (potato extract 4.0 g/L, casein/meat peptone 2.0 to 3.0 g/L, glucose 24.0 to 26.0 g/L, agar 15.0 g/L), and a medium blended with a PDA medium in an amount of 22.5 to 27.5% by mass (potato extract 4.0 g/L, casein/meat peptone 2.25 to 2.75 g/L, glucose 24.5-25.5 g/L, agar 15.0 g/L) is more preferable.

The membrane filter obtained in the filtering step is attached to the surface of a plate medium and cultured for a predetermined period of time to allow the living microorganisms on the membrane filter to proliferate and form colonies. Culture time is preferably 3 to 36 hours, more preferably 3 to 24 hours, and even more preferably 12 to 24 hours. The culture temperature may be within a temperature range in which mold, yeast, and bacteria can proliferate, and the culture can be carried out, for example, within a range of 20 to 35° C. From the viewpoint of being able to sufficiently grow heat-resistant molds that are considered to be harmful microorganisms that may be mixed into industrial products such as beverages while avoiding the risk of poor growth of general environmental bacteria, the culture temperature is preferably 20 to 35° C., more preferably to 32° C., even more preferably 28 to 32° C., and particularly preferably 30° C.

[Fluorescent Staining Step]

After the culturing step, the membrane filter peeled off from the plate medium is brought into contact with a staining agent for fluorescently staining microorganisms to fluorescently stain the microorganisms on the membrane filter. The staining agent for fluorescently staining microorganisms is not particularly limited as long as it is capable of fluorescently staining living microorganisms, and it may be one that stains only live bacteria, or may be one that stains both live bacteria and dead bacteria. The staining agent is preferably one that stains only live bacteria, since it is possible to suppress noise caused by lactic acid bacteria, yeast, etc. that are added as raw materials for beverages and killed during sterilization.

By focusing on the physiological activity of microorganisms and using a staining agent that fluorescently stains only live bacteria having the relevant physiological activity, it is possible to fluorescently stain only the live bacteria without staining the dead bacteria. Examples of the fluorescent staining agent include non-fluorescent molecules that are decomposed by the esterase activity or oxidoreductase activity of live bacteria to produce fluorescent molecules. Examples of the fluorescent staining agent utilizing esterase activity include CFDA (6-carboxyfluorescein diacetate), CFDA-AM (carboxyfluorescein diacetate-acetoxymethlester), FDA (fluorescein diacetate), Calcein-AM (calcein-acetoxymethlester) and the like. Non-fluorescent CFDA taken into the microbial body of the microorganism is converted into 6-carboxyfluorescein, which emits green fluorescence by esterase activity within the microorganisms. Examples of the fluorescent staining agent utilizing oxidoreductase activity include CTC (5-cyano-2,3-ditolyl tetrazolium chloride), which is a monotetrazolium reducing dye. The non-fluorescent CTC taken into the microbial body of the microorganism is reduced by the electron transfer system associated with respiration in the microorganism and converted into CTF (CTC formazan), which emits red fluorescence.

In addition, many non-living organisms such as amino acids, peptides, dietary fibers and the like do not contain nucleic acids, or even if they do, the amount is extremely small. Therefore, it is possible to fluorescently stain the microorganisms while suppressing non-biological noise using a nucleic acid fluorescent staining agent. Examples of the nucleic acid fluorescent staining agent include acridine orange, DAPI (4',6-diamido no-2-phenylindole), ethidium bromide, PI (propidium iodine), Hoechst 33258, Hoechst 33342, SYBR Green and the like. Many of the nucleic acid staining agents also stain the dead bacteria, but the dead bacteria do not proliferate and do not form colonies, so the dead bacteria and the live bacteria can also be distinguished based on the brightness value, size, shape, etc. of the bright spots in the fluorescence image.

Many autofluorescent substances, such as amino acids and dietary fibers, emit strong fluorescence when exposed to light with a short wavelength, such as ultraviolet rays. For this reason, harmful microorganisms are preferably stained with a fluorescent staining agent that emits fluorescence with excitation light of a relatively long wavelength, particularly a fluorescent staining agent that emits green to red fluorescence. This makes it possible to reduce the fluorescence signals derived from noise components in the fluorescence image and reduce noise.

Specifically, the membrane filter peeled off from the plate medium is immersed in a fluorescent staining agent solution. The fluorescent staining agent solution is prepared by dissolving a fluorescent staining agent in a solvent such as water or a buffer. The buffer used as a solvent is not particularly limited, and phosphate saline (PBS), tris buffer, phosphate buffer, HEPES buffer, dimethyl sulfoxide (DMSO) and the like can be used. Immersion in the fluorescent staining agent solution can be carried out, for example, by incubation at 4 to 38° C., preferably 30 to 37° C., for 5 minutes to 6 hours.

[Imaging Step]

After the fluorescent staining step, a fluorescence image of the fluorescently stained membrane filter is imaged. The fluorescence image can be imaged by irradiating excitation light suitable for the fluorescent staining agent used for the fluorescent staining and detecting the generated fluorescence signals using a fluorescence imaging device equipped with an imaging device such as a CCD camera. As the fluorescence imaging device, commercially available imaging devices capable of detecting fluorescence signals, which are used for detecting colonies of cells or microorganisms, can be used.

As for the fluorescence image of each membrane filter, only one image may be imaged for the same field of view, or several images may be imaged at intervals. For example, by acquiring fluorescence images in the same field of view at the early and late stages of fluorescent staining, information on changes in fluorescence signals over time can also be acquired. Harmful microorganisms and noise components often have different temporal changes in the fluorescence reaction. Therefore, it is possible to distinguish between the fluorescence signals derived from the harmful microorganisms and the noise components in the fluorescence image with a higher accuracy using the temporal change information of the fluorescence signals.

[Learning Data Generation Step]

In the fluorescence image, the living harmful microorganisms and the noise components differ in fluorescence signal intensity (brightness value), shape, size, each RGB brightness value, changes in fluorescence intensity depending on staining time, and the like. Based on these differences, fluorescence signals derived from the harmful microorganisms in the fluorescence image can be distinguished from the fluorescence signals derived from the noise components (noise), and the harmful microorganisms can be detected with high accuracy.

If the culture time on the membrane filter is short, the colonies formed by the microorganisms are also small, and although the detection sensitivity can be increased by fluorescent staining, in many cases the shape and fluorescence signal intensity are similar to the noise components, making it difficult to distinguish between the two. Conventionally, humans have visually identified the two, and the accuracy of identification depends on the skill level of the person identifying them, and it also takes time to determine the presence or absence of the harmful microorganisms. In the method for detecting microorganisms according to the embodiment of the present disclosure, machine learning, especially deep learning, is performed to determine the difference in feature values between the fluorescence signals derived from the harmful microorganisms and the noise components to generate an algorithm for distinguishing between the two. By using a trained model equipped with the generated algorithm, it is possible to distinguish between the fluorescence signals derived from the harmful microorganisms and the noise in the fluorescence images acquired from the liquid test sample in a very short time with a stable distinction accuracy, thereby improving the microorganism detection accuracy.

Learning data for generating a trained model (hereinafter referred to as "trained model for detecting microorganisms") for distinguishing between the fluorescence signals derived from the harmful microorganisms and the noise is prepared using, for example, a liquid obtained by adding harmful microorganisms of known biological species to a liquid of the same type as the liquid test sample (microorganism-inoculated liquid sample). In addition, the feature values such as the brightness value of the fluorescence signals derived from the harmful microorganisms and the noise are affected by the type and amount of the noise components contained in the liquid test sample, the culture conditions of the membrane filter, the type and staining conditions of the fluorescent staining agent, the imaging conditions of the fluorescence image and the like. For this reason, the trained model is preferably generated by performing deep learning using learning data obtained under the same conditions as those for the actual detection of microorganisms.

The harmful microorganisms added to the same type of liquid as the test liquid sample may be filamentous fungi, yeast, or bacteria. Also, the type of harmful microorganisms added to the liquid may be one, or two or more. For example, a microorganism-inoculated liquid sample to which heat-resistant fungi, yeast, and bacteria are all added can be used. The microorganism-inoculated liquid sample is preferably a liquid sample containing filamentous fungi (molds), whose colonies are irregular and relatively difficult to distinguish from the noise in a fluorescence image. Liquid samples containing yeast that can grow in acidic carbonated beverages are also preferable, and liquid samples containing heat-resistant fungi and heat-resistant yeast, which tend to cause problems in sterilized packaged beverages, are also preferable. As the yeast that can grow in acidic carbonated drinks, *Saccharomyces cerevisiae, Zygosaccharomyces fermentati, Candida krusei, Torulaspora delbrueckii, Zygosaccharomyces bailii*, etc., which are suitable as contamination indicator bacteria for acidic carbonated drinks, are more preferable. As the heat-resistant mold, *Byssochlamys fulva, Aspergillus fischeri, Talaromyces flavus, Hamigera avellanea*, etc., which are suitable as contamination indicator bacteria for acidic non-carbonated beverages, are more preferable.

The fluorescence signals in the fluorescence image of the microorganism-inoculated liquid sample include both the fluorescence signals derived from the harmful microorganisms and the noise. Therefore, the fluorescence signals derived from the harmful microorganisms are marked in the fluorescence image of the microorganism-inoculated liquid sample, and the model is made to learn that the marked fluorescence signals are the fluorescence signals derived from the harmful microorganisms. It is preferable that the membrane filter prepared from the microorganism-inoculated liquid sample be re-attached to the plate medium after imaging fluorescence images and cultured continuously until the colonies are visually recognized, thereby confirming that the fluorescence signals in the marked area of the membrane filter prepared from the microorganism-inoculated liquid sample are the fluorescence signals derived from the harmful microorganisms.

In addition, the fluorescence images used for learning data and the fluorescence images for marking the fluorescence signals derived from the harmful microorganisms may be separately prepared. For example, after acquiring a fluorescence image of the membrane filter in the imaging step after the fluorescent staining step, the membrane filter is re-attached to the plate medium and cultured continuously until the colonies can be visually recognized, and then a fluorescence image of the same field of view is acquired again. The microorganism location information obtained by marking the fluorescence signals derived from the harmful microorganisms on the fluorescence image of the membrane filter after continuous culture can be combined with the fluorescence image first acquired after the fluorescence staining step to be used as learning data.

Specifically, for the fluorescence images obtained from each of the multiple membrane filters that filtered the microorganism-inoculated liquid sample, microorganism position information indicating the position of the harmful microorganisms on the fluorescence image is input, and the fluorescence image and the microorganism position information are generated as learning data. By performing deep learning using this learning data, a trained model for detecting microorganisms is generated. Although the learning amount for generating a trained model for detecting microorganisms that has sufficient ability to distinguish between the fluorescence signals derived from the harmful microorganisms and the noise is not particularly limited, it is preferable to perform deep learning on learning data in which the number of marked areas in the fluorescent image of the microorganism-inoculated liquid sample is 300 or more.

As a learning tool, one or a combination of two or more image analysis tools that are widely used for image analysis of fluorescence images can be used. Examples of the image analysis tool include a defect detection tool (hereinafter sometimes referred to as "Red tool") that detects mutations (e.g., cracks and chips) in an image, a position detection tool (hereinafter sometimes referred to as a "Blue tool") that detects and counts specific objects (e.g., human), and a classification tool (hereinafter sometimes referred to as a "Green tool") that classifies detected objects. These can be used in combination.

In addition to the learning using the fluorescence images of microorganism-inoculated liquid samples, it is also preferable to perform learning (non-defective product learning) using, as learning data, a fluorescent image of a liquid (blank sample) that is the same type of liquid as the liquid test sample and is confirmed to contain no harmful microorganisms. The fluorescence signals in the fluorescent image of the blank sample are all noise, and by performing non-defective product learning, the ability of the trained model for detecting microorganisms to distinguish between fluorescence signals derived from harmful microorganisms and noise can be further improved, and the false positive rate can be further reduced.

[Inspection Step]

The presence or absence of the harmful microorganisms is determined using the generated trained model for detecting microorganisms on the fluorescence images prepared from the liquid test sample input as the inspection target. The trained model for detecting microorganisms identifies whether the fluorescence signal of each pixel in the fluorescence images is a fluorescence signal derived from the harmful microorganisms or the noise. If it is determined that the fluorescence image includes a fluorescence signal derived from the harmful microorganisms, it is determined that the liquid test sample contains harmful microorganisms. That is, the harmful microorganisms in the liquid test sample are detected as a fluorescence signal derived from the harmful microorganisms in the fluorescence image.

[Trained Model for Detecting Microorganisms]

FIG. 1 is a schematic diagram showing a display example of inspection results according to an embodiment of the present disclosure. The inspection results are displayed on the screen of an inspection device 2, which will be described later. On the screen, the types and positions of the molds are shown for the imaged fluorescence image, and the quality determination results are also shown.

Display examples G11, G12, and G13 are display example G11 when no harmful microorganisms are detected, display example G12 when harmful microorganism A is detected, and display example 13 when harmful microorganism B is detected, respectively, in the fluorescence images of the liquid containing many noise components.

Although many noise components were present in display example G11, no harmful microorganisms were detected. The quality determination was also good. In display example G12, harmful microorganism A was detected, and the colony positions of harmful microorganism A were colored. In display example G13, harmful microorganism B was detected, and the colony positions of harmful microorganism A were colored.

Due to the fluorescent reaction between the harmful microorganisms and the noise components, there was a large difference in the harmful microorganisms and their types, or in the noise components on the image compared to when there was no fluorescent reaction. The inspection device 2 was able to distinguish the harmful microorganisms and their types from the noise components, thereby making it possible to identify the type and location of the molds, and also perform the quality determination with high accuracy.

Figure 2:
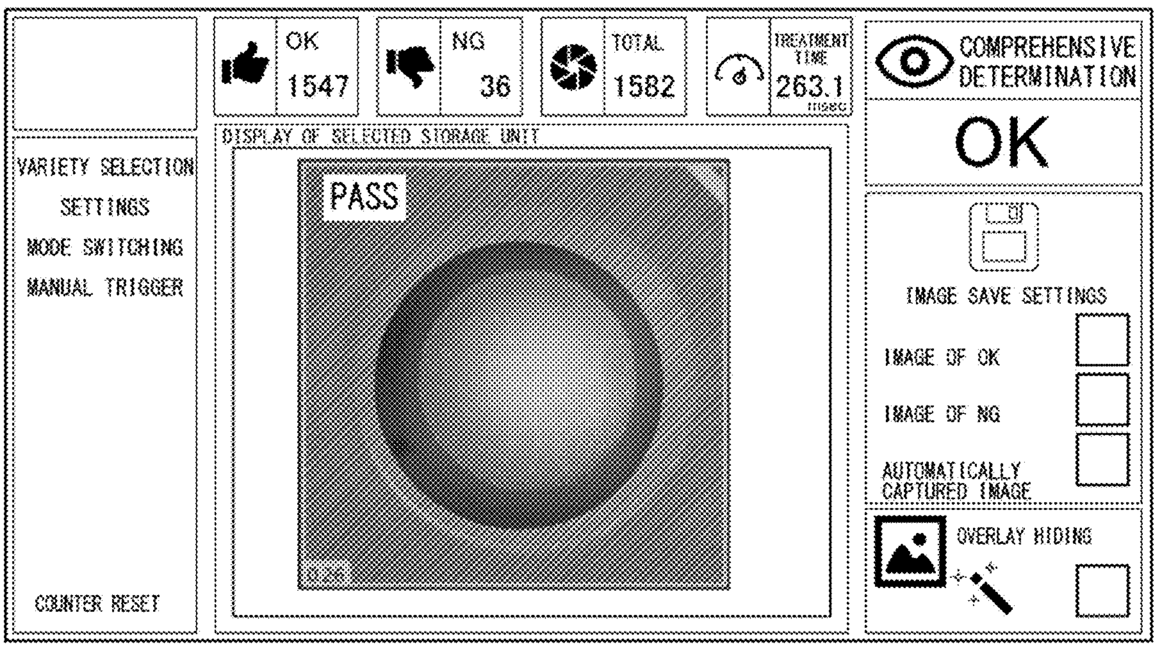
FIG. 2 is a schematic diagram showing an example of the inspection screen according to the present embodiment.

FIG. 2 is a schematic diagram showing an example of the inspection screen according to the embodiment.

This inspection screen displays a menu for variety selection, settings, mode switching, manual trigger, etc., inspection results (see FIG. 1), evaluation of inspection results such as OK, NG, total number, processing time, etc., comprehensive determination, save settings and overlay display settings.

The variety selection is a menu for selecting a variety. The variety is the type of the liquid test sample. When the type of liquid test sample is a beverage, for example, it is a milky drink, a carbonated milky drink, a fruit juice drink, etc., a type to which the liquid test sample corresponds is selected from the group of types registered in advance.

"OK" is the number of images of non-defective products (no harmful microorganisms detected), and "NG" is the number of images of defective products (with harmful microorganisms detected). The total number is the cumulative number of images of non-defective products and images of defective products (total number of inspection results).

The comprehensive determination displays the quality determination result. In this figure, "OK" (non-defective product) is displayed.

<System Configuration>

The inspection system S includes a learning device 1 and the inspection device 2. The learning device 1 performs a machine learning process based on a plurality of fluorescence images and microorganism position information indicating the positions of the harmful microorganisms in each fluorescence image. The learning device 1 generates a trained model as a result of the machine learning process.

The inspection device 2 uses the trained model generated by the learning device 1 to determine the presence or absence of the harmful microorganisms for each pixel (position) of the input fluorescence image (also referred to as "inspection fluorescence image"). If a harmful microorganism is present in the inspection fluorescence image, the inspection device 2 generates display data in which the position of the harmful microorganism is colored, and displays the data on the display (see FIGS. 1 and 2).

<Structure of Learning Device>

Figure 3:
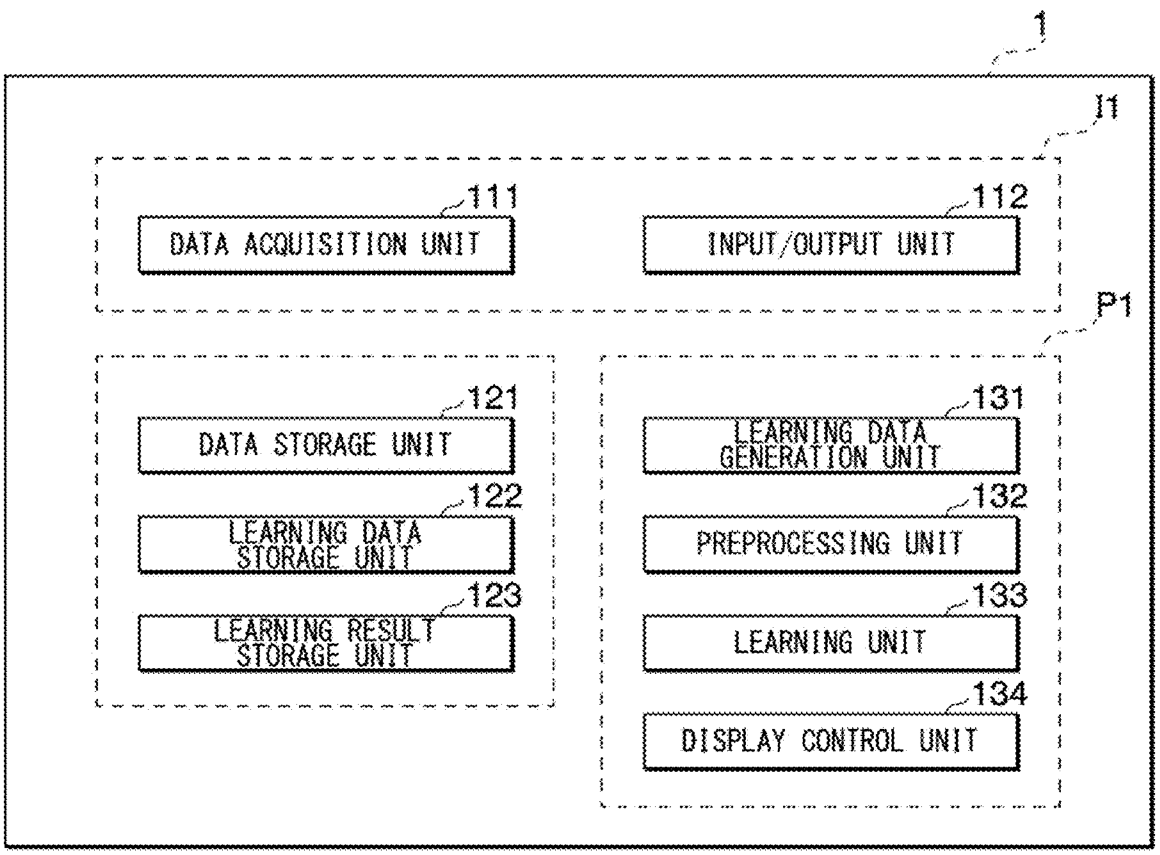
FIG. 3 is a schematic block diagram showing a configuration of the learning device according to the present embodiment.

FIG. 3 is a schematic block diagram showing the configuration of the learning device 1 according to the embodiment.

The learning device 1 includes an input/output unit I1, a memory unit M1, and a processing unit P1.

The input/output unit I1 includes a data acquisition unit 111 and an input/output unit 112.

The data acquisition unit 111 acquires data from communication or an external storage device.

The input/output unit 112 receives information by user operations such as keyboard input and marking using a pointing device.

The memory unit M1 includes a data storage unit 121, a learning data storage unit 122 and a learning result storage unit 123.

The data storage unit 121 stores the data acquired by the data acquisition unit 111. The data includes fluorescence images and additional information for each of the plurality of the fluorescence images, and the additional information includes sample information and culture information. The sample information is information regarding the sample to be inspected, such as the type (variety) and name of the target liquid sample, noise component information (noise components and their types), microorganism information (classification of harmful microorganisms (filamentous fungus, yeast, bacteria) and biological species), manufacturing information (factory, line, raw material, manufacturing date, etc.), storage information, etc. The culture information is information regarding the culture of the sample, and includes culture medium information, membrane information (diameter or pore size), and detection work information (reagent or its type, reagent immersion time, fluorescence imaging time, etc.).

The learning data storage unit 122 stores learning data used for machine learning. The learning data is data obtained by adding microorganism position information to each fluorescence image and its additional information.

The learning result storage unit 123 stores a trained model generated as a result of the machine learning process based on the learning data.

The processing unit P1 includes a learning data generation unit 131, a preprocessing unit 132, a learning unit 133 and a display control unit 134.

The learning data generation unit 131 displays the fluorescence image on the display to allow the user to generate the learning data. The learning data generation unit 131 receives microorganism information and microorganism position information for each pixel through a user operation on each displayed fluorescence image.

The learning data generation unit 131 generates, for each pixel of each of the plurality of fluorescence images, pixel information of the fluorescence image, microorganism information, and microorganism position information as learning data. Here, the pixel information is an RGB value, but may also be a brightness value, a gray scale, or a binary value. The learning data generation unit 131 stores the generated learning data in the learning data storage unit 122.

The preprocessing unit 132 performs preprocessing such as processing before machine learning on the learning data. For example, the preprocessing unit 132 performs noise removal processing based on the membrane information to remove a portion (edge portion) that is a certain distance or more from the center of the membrane filter. During the filtration process, liquid does not pass through the vicinity of the membrane filter's boundaries, and theoretically, no harmful microorganisms or noise components exist. If the fluorescent signals in the area through which the liquid has not penetrated are determined to be fluorescent signals derived from harmful microorganisms, the false positive rate will increase. By this noise removal process, the vicinity of the boundary of the membrane filter is removed, thereby making it possible to prevent the inspection device 2 from erroneously determining the harmful microorganisms or noise components.

The learning unit 133 performs the machine learning process based on the learning data preprocessed by the preprocessing unit 132. Specifically, the learning unit 133 performs the machine learning process using a CNN (convolutional neural network) as a learning model, pixel information of a fluorescence image as an objective variable, and microorganism information and microorganism position information as explanatory variables. The learning unit 133 stores the generated trained model in the learning result storage unit 123. Details of the machine learning process will be described later.

The display control unit 134 generates screen data for generating a screen. The display control unit 134 displays the screen on the user's display by outputting the generated screen data via the input/output unit 112.

<Generation of Learning Data>

Figure 4:
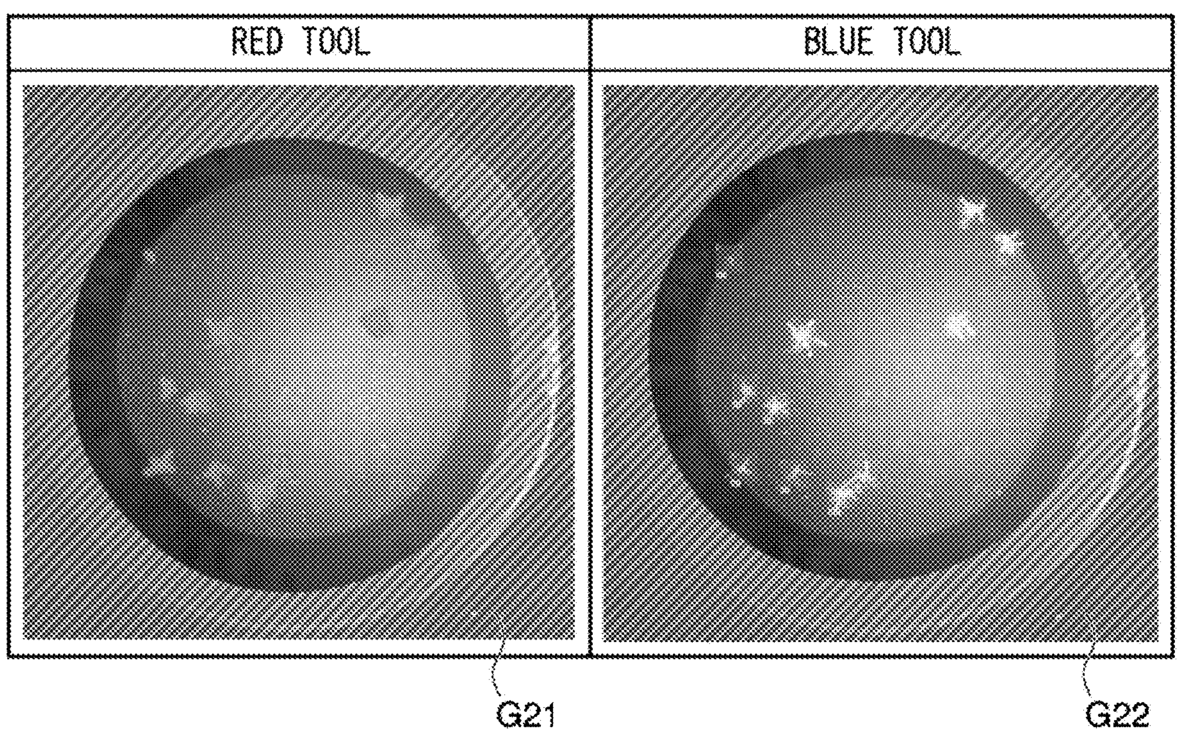
FIG. 4 is a schematic diagram showing an example of a user operation according to the present embodiment.

FIG. 4 is a schematic diagram showing an example of the user operation according to the embodiment. This user operation includes an operation of designating microorganism position information for each displayed fluorescence image, which is an operation that allows the user to generate learning data. This operation is for the user to mark the harmful microorganisms.

Display examples G21 and G22 are display examples when the harmful microorganisms are marked on the fluorescence images with the Red tool and the Blue tool, respectively. The markings in display example G21 are those in which the user has filled out harmful microorganisms (including those in the vicinity). The markings in display example G22 are those in which the user has enclosed harmful microorganisms in a rectangle.

When a marking like the display example G21 or G21 is made, the learning data generation unit 131 identifies pixels within the marking whose brightness is higher than the threshold value as the position (pixel) where the target harmful microorganism exists. The learning data generation unit 131 uses the identified position as the microorganism position information, and generates learning data in which the pixel information of the fluorescence image, the microorganism information, and the microorganism position information are combined. Here, the learning data generation unit 131 receives markings for each piece of microorganism information, and generates learning data for each piece of target microorganism information using the microorganism information and the microorganism position information as explanatory variables.

<Process of Learning Device>

The process of the learning device 1 will be described below with each unit in FIG. 3 as the processing subject.

Figure 5:
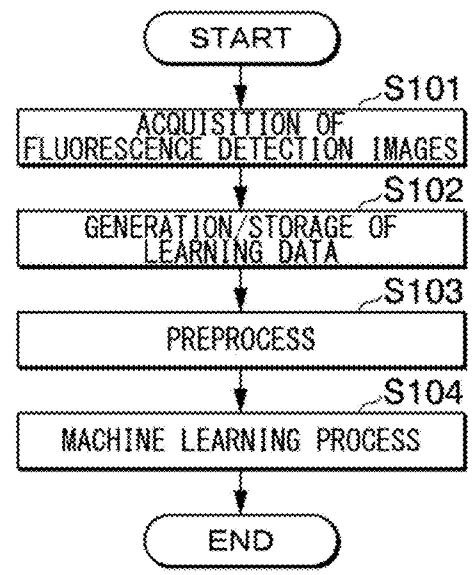
FIG. 5 is a flowchart showing an example of a process of the learning device according to the present embodiment.

FIG. 5 is a flowchart showing an example of a process of the learning device 1 according to the embodiment.

(Step S101)

The data acquisition unit 111 acquires a plurality of fluorescence images and additional information. After that, the process of step S102 is performed.

(Step S102)

The learning data generation unit 131 displays each fluorescence image and additional information acquired in step S101, and allows the user to mark the harmful microorganisms for each microorganism information (see FIG. 4). The learning data generation unit 131 identifies the microorganism position information based on the markings, and generates learning data in which the pixel information of the fluorescence image, the microorganism information, and the microorganism position information are combined. The learning data generation unit 131 stores the generated learning data in the learning data storage unit 122. After that, the process of step S103 is performed.

(Step S103)

The preprocessing unit 132 performs preprocessing such as noise removal processing or the like on the learning data stored in step S102. After that, the process of step S104 is performed.

(Step S104)

The learning unit 133 performs the machine learning process based on the learning data preprocessed in step S103. A trained model is generated as a result of the machine learning process.

<Configuration of Inspection Device>

Figure 6:
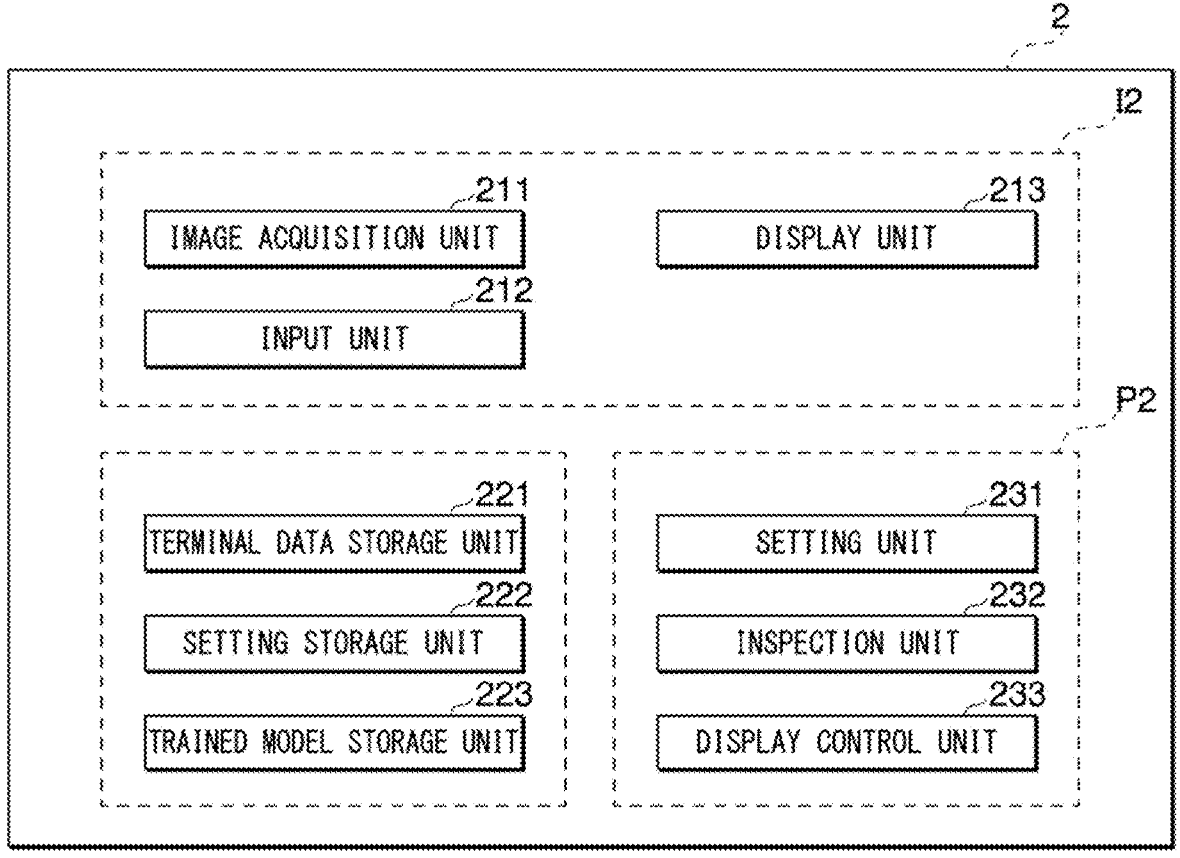
FIG. 6 is a schematic block diagram showing a configuration of the inspection device according to the present embodiment.

FIG. 6 is a schematic block diagram showing the configuration of the inspection device 2 according to the embodiment.

The inspection device 2 includes an input/output unit 12, a memory unit M2, and a processing unit P2.

The input/output unit 12 includes an image acquisition unit 211, an input unit 212 and a display unit 213.

The image acquisition unit 211 acquires an inspection fluorescence image as an inspection target from an imaging device, communication, or an external storage device.

The input unit 212 receives information by a user operation through keyboard input or a pointing device.

The display unit 213 is a display, and displays inspection results and the like (see FIG. 1).

The memory unit M2 includes a terminal data storage unit 221, a setting storage unit 222 and a trained model storage unit 223.

The terminal data storage unit 221 stores the inspection fluorescence image acquired by the image acquisition unit 211, the information received by the input unit 212, and the inspection result of the inspection unit 232.

The setting storage unit 222 stores inspection setting information. The setting information includes, for example, a threshold value T1 for determining the presence or absence of harmful microorganisms and a threshold value T2 used for quality determination.

The trained model storage unit 223 stores the trained model generated by the learning device 1.

The processing unit P2 includes a setting unit 231, an inspection unit 232 and a display control unit 233. The setting unit 231 allows the user to input the setting information such as the threshold value T1 and the threshold value T2 to store the setting information in the setting storage unit 222.

The inspection unit 232 uses the trained model stored in the trained model storage unit 223 to determine the presence or absence of harmful microorganisms in the input inspection fluorescence image (inspection process). The determination result of the presence or absence of harmful microorganisms includes the position information of the microorganisms in the inspection fluorescence image or the determination result of quality determination. The quality determination means that the inspection unit 232 calculates the total area of harmful microorganisms or the size or number of the colonies based on the microorganism position information, and uses the calculated result and the threshold value T2 to determine the quality of the liquid (presence or absence of harmful microorganisms). Further, the presence or absence of harmful microorganisms is determined based on the probability of the microorganism position information output from the trained model and the threshold value T1.

The display control unit 233 allows the display unit 213 to display the inspection results including the determination result of the presence or absence of harmful microorganisms.

<Process of Inspection Device>

The process of the inspection device 2 will be described below with each unit shown in FIG. 6.

Figure 7:
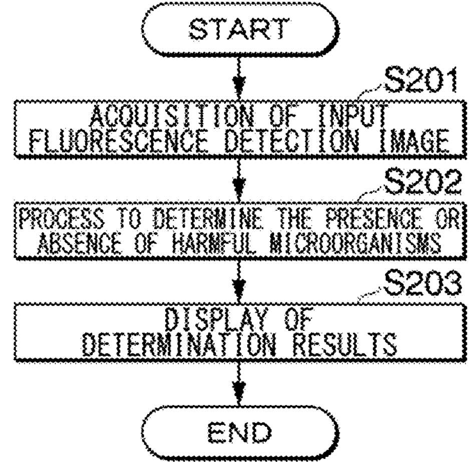
FIG. 7 is a flowchart showing an example of a process of the execution device according to the present embodiment.

FIG. 7 is a flowchart showing an example of a process of the inspection device 2 according to the embodiment.

(Step S201)

The image acquisition unit 211 acquires an inspection fluorescence image as an inspection target. After that, the process of step S201 is performed.

(Step S202)

The inspection unit 232 uses the trained model generated by the machine learning process (step S104 in FIG. 5) to determine the presence or absence of harmful microorganisms in the inspection fluorescence image acquired in step S201. After that, the process of step S203 is performed.

(Step S203)

The display control unit 233 allows the display unit 213 to display the determination result (inspection result) of the presence or absence of harmful microorganisms in step S202.

In addition, the inspection device 2 may include the preprocessing unit 132 of the learning device 1, and may perform a noise removal processing similar to that of the learning device 1 after step S201.

<Regarding Machine Learning Process and Inspection Process>

The machine learning process will be described below.

The learning unit 133 performs the machine learning process using the pixel values of the fluorescence image and the learning data set of the microorganism information and the microorganism position information. Specifically, the learning unit 133 uses the pixel values of the preprocessed fluorescence image as input variables to be input to the input layer for a learning CNN (convolutional neural network). The learning unit 133 sets the microorganism information and the microorganism position information as output variables output from the output layer. Here, the learning unit 133 sets a value representing each microorganism information (for example, "1" for harmful microorganism A and "2" for harmful microorganism B) for the pixel indicated by the microorganism position information. However, the present invention is not limited to this, and the learning unit 133 may perform the machine learning process on a CNN determined for each microorganism information or additional information (for example, variety). For example, the learning device 1 generates learning data for each milky drink, carbonated milky drink, or fruit juice drink, and performs the machine learning process on the CNN using each of the learning data to generate each trained model. The inspection device 2 may use a trained model corresponding to any one of the milky beverage, carbonated milky beverage, or fruit juice selected by the user to determine the presence or absence of harmful microorganisms. The properties and contaminants of the liquid test samples differ depending on the variety, and also the harmful microorganisms that may be present differ depending on the variety. Therefore, the image resulting from fluorescent staining may vary greatly depending on the liquid test sample. In this case, it is possible that the inspection system S generates learning data and a trained model for each variety, and uses the trained model for each type of liquid test sample to determine the presence or absence of harmful microorganisms, thereby improving the accuracy of this determination.

Figure 8:
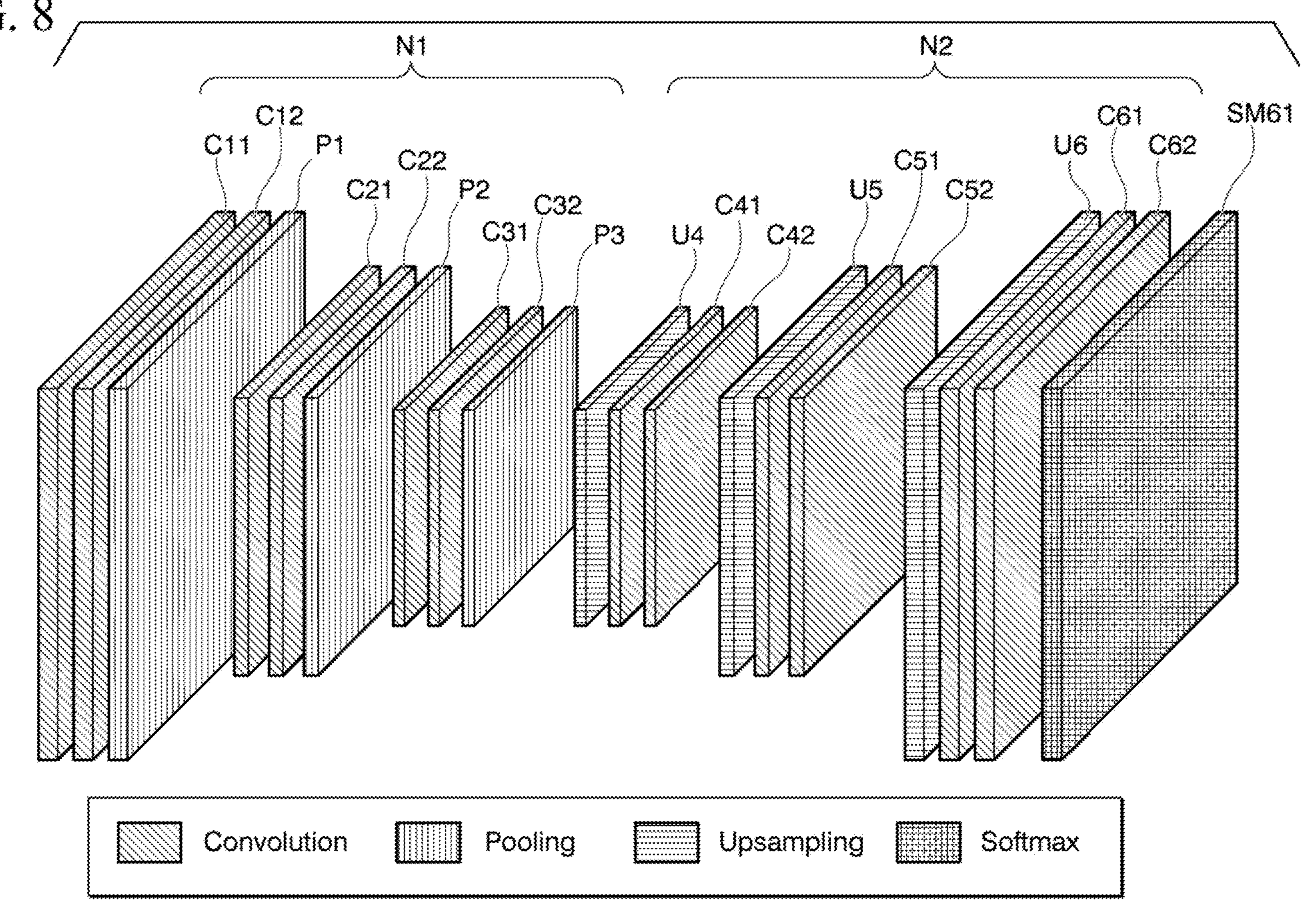
FIG. 8 is a schematic diagram showing an example of a machine learning process according to the present embodiment.

FIG. 8 is a schematic diagram showing an example of the machine learning process and inspection process.

This schematic diagram shows a method called SegNet among the image segmentation neural networks.

In this schematic diagram, the neural networks N1 and N2 are symmetrical. In the neural network N1, a convolution process (computation) and a pooling process are repeated. The convolution process is a process of filtering the original image and outputting a feature map, and the pooling process is a process of reducing the image while retaining the image features. The convolution process may include normalization processing such as batch normalization or the like. First, a convolution process C11, a convolution process C12, and a pooling process P1 are performed on an input variable (pixel value). After that, a convolution process C21, a convolution process C22, a pooling process P2, a convolution process C31, a convolution process C32, and a pooling process P3 are performed. The results of these processes are input to the neural network N2.

In the neural network N2, an upsampling process and a (de)convolution process are repeated. The upsampling process is a process of enlarging an image that has been reduced by the pooling process. An upsampling process U4, a convolution process C41, and a convolution process C42 are performed on the processing result of the neural network N1. Thereafter, an upsampling process U5, a convolution process C51, a convolution process C52, an upsampling process U6, a convolution process C61, and a convolution process C62 are performed.

In the machine learning process, a softmax process SM is not performed, but the error between the output of the convolution process C62 and the output variable is calculated, and a back propagation process is performed based on the error. In the inspection process, softmax processing SM is finally performed.

In addition, in the neural network of the present invention, the convolution process and pooling process (upsampling process) may be performed another number of times, or some of them may not be performed. Also, in the machine learning process and inspection process of the present invention, another method may be used, and for example, it may be FCN (Fully Convolutional Network), U-Net, PSPNet (Pyramid Scene Parsing Network). In addition, in the machine learning process and the inspection process, a sigmoid function may be set as the activation function of all layers, and other activation functions such as a step function, linear combination, soft sine, soft plus, ramp function, cutting power function, polynomial, absolute value, radial basis function, wavelet, maxout or the like may be set as the activation function of each layer. In addition, the activation function for a certain layer may be of a different type than of other layers.

In the machine learning process, a squared loss (mean squared error) may be set as an error function, and cross entropy, t-quantile loss, Huber loss, and & sensitivity loss (& tolerance function) may also be set as an error function. In the machine learning process, SGD (stochastic gradient descent) is set as an algorithm for calculating gradients (gradient descent algorithm). However, the present invention is not limited to this, and Momentum (inertia term) SDG, AdaGrad, RMSprop, AdaDelta, Adam (Adaptive moment estimation) or the like may be used for the gradient descent algorithm. In the machine learning processing and inspection processing, not only may a convolutional neural network (CNN) be set but also other neural networks such as a perceptron neural network, a recurrent neural network (RNN), and a residual network (ResNet) may be set.

<Summary of Each Device>

As described above, the learning device 1 reads, as learning data, fluorescence images obtained by imaging a membrane filter cultured with microorganisms collected from a liquid and fluorescently stained with a fluorescent staining agent for microorganisms and microorganism position information indicating the microorganism positions on the fluorescence images, and generates a trained model by performing machine learning based on the learning data. The inspection device 2 determines the presence or absence of harmful microorganisms in fluorescence images input as an inspection target using a trained model generated by performing machine learning based on fluorescence images obtained by imaging a membrane filter cultured with microorganisms collected from a liquid and fluorescently stained with a fluorescent staining agent for harmful microorganisms and microorganism position information indicating the microorganism positions on the fluorescence images.

Here, the trained model is a trained model for detecting harmful microorganisms in a liquid, which is generated by performing machine learning based on fluorescence images obtained by imaging a membrane filter cultured with microorganisms collected from a liquid and fluorescently stained with a fluorescent staining agent for harmful microorganisms and microorganism position information indicating the harmful microorganism positions on the fluorescence images, and allows a computer to function to determine the presence or absence of the harmful microorganisms in the fluorescence image input as the inspection object.

As a result, the inspection system S can rapidly and highly sensitively detect harmful microorganisms in liquids containing various components.

For example, when determining harmful microorganisms with the human eye, it may not be possible to determine the presence of harmful microorganisms without culturing them for two or more days. On the other hand, the inspection system S may be able to determine the presence or absence of harmful microorganisms even after culturing for about one day (for example, within 36 hours). In other words, the inspection system S may be able to determine the presence or absence of harmful microorganisms even if the colony of the harmful microorganisms is smaller than the size that allows the human eye to accurately determine the harmful microorganisms (for example, 1 mm or less).

Furthermore, the learning device 1 removes the edge portion of the membrane filter from the fluorescence image. The learning device 1 performs machine learning based on the fluorescence image from which the edge portion of the membrane filter has been removed and the microorganism position information. As a result, the inspection system S can remove the vicinity of the boundary of the membrane filter through this noise removal process, and can prevent the inspection device 2 from erroneously determining harmful microorganisms or noise components.

Further, the learning device 1 performs machine learning based on a fluorescence image imaged by irradiating excitation light of a fluorescent staining agent used for fluorescent staining. The inspection device 2 determines the presence or absence of harmful microorganisms (inspection results) on the fluorescence image imaged by irradiating the excitation light of the fluorescent staining agent used for the fluorescence staining. As a result, harmful microorganisms are fluorescently stained, making it easier to distinguish between the harmful microorganisms and the noise components such as contaminants that emit self-luminescence, and the inspection system S can accurately determine the presence or absence of harmful microorganisms even if the culture time is shorter than when determining the presence or absence of harmful microorganisms with the human eye.

Further, the plate medium contains glucose, peptone, and potato extract, and the peptone concentration is 2-5 g/L. Preferably, the plate medium consists only of glucose, peptone, potato extract and agar. As a result, it is possible to achieve both noise reduction and promotion of the growth of microorganisms, and the inspection system S can accurately determine the presence or absence of harmful microorganisms even if the culture time is shorter than when determining the presence or absence of harmful microorganisms with the human eye.

EXAMPLES

Next, the present invention will be described in more detail with reference to Examples and the like, but the present invention is not limited to the following Examples and the like.

Reference Example 1

A trained model for detecting harmful microorganisms in a milky non-carbonated beverage was developed. In order to generate learning data, heat-resistant mold *B. fulva* was added to a milky non-carbonated drink of the same type as the liquid test sample at a concentration of 20 cfu per membrane filter used for filtration, and this was used as a heat-resistant mold-inoculated beverage. Further, a milky non-carbonated beverage of the same type as the liquid test sample, which was confirmed to contain no viable bacteria, was used as a blank beverage.

<Optimization of Culture Medium>

First, the heat-resistant mold-inoculated beverage was filtered through a membrane filter ("MF-Millipore (AABP02500)", manufactured by Merck), and then the membrane filter was attached to the surface of a plate medium and cultured at 25° C. or 30° C. for 24 hours. As the plate medium, a plate medium prepared by adding agar to Sabouraud's glucose liquid medium rich in nitrogen sources ("Daigo", for Japanese Pharmacopoeia testing, manufactured by Nihon Pharmaceutical Co., Ltd.) (hereinafter sometimes referred to as "Sabouraud medium") was used so that the heat-resistant molds collected on the membrane filter could grow sufficiently in 24 hours.

A CFDA staining reagent (product name "EzFluo Reagent Kit", manufactured by Merck) was added to the membrane filter peeled from the plate medium after culturing in an amount recommended by the manufacturer, and incubated at 30° C. for 5 minutes for staining. A green fluorescence image of the fluorescence-stained membrane filter was imaged using a fluorescence imaging device (trade name "TM-LABplus", manufactured by Tsuchiya Co., Ltd.).

As a result, the acquired green fluorescence image was not suitable for image analysis because abnormal luminescence occurred throughout the membrane and colony halation occurred in the center of the image.

It was speculated that the abnormal luminescence and the halation in the fluorescence image were caused by the autofluorescence of amino acids abundantly contained in the medium. Therefore, fluorescence images of the heat-resistant mold-inoculated beverage and blank beverage were prepared in the same manner, except that PDA agar medium (manufactured by Nissui Pharmaceutical Co., Ltd.), which contains few autofluorescent components, was added with various amounts of Sabouraud medium. As a result, the plate medium in which 7.5 g/L of Sabouraud medium was mixed with a PDA agar medium (manufactured by Nissui Pharmaceutical Co., Ltd.) (4.0 g/L potato extract, 2.5 g/L casein/meat peptone, 25.0 g glucose/L, agar 15.0 g/L) (hereinafter, referred to as "PS25 plate medium") allowed the growth of heat-resistant molds to be sufficiently fast, and made it possible to obtain fluorescence images suitable for image analysis without abnormal luminescence or halation.

Figure 9:
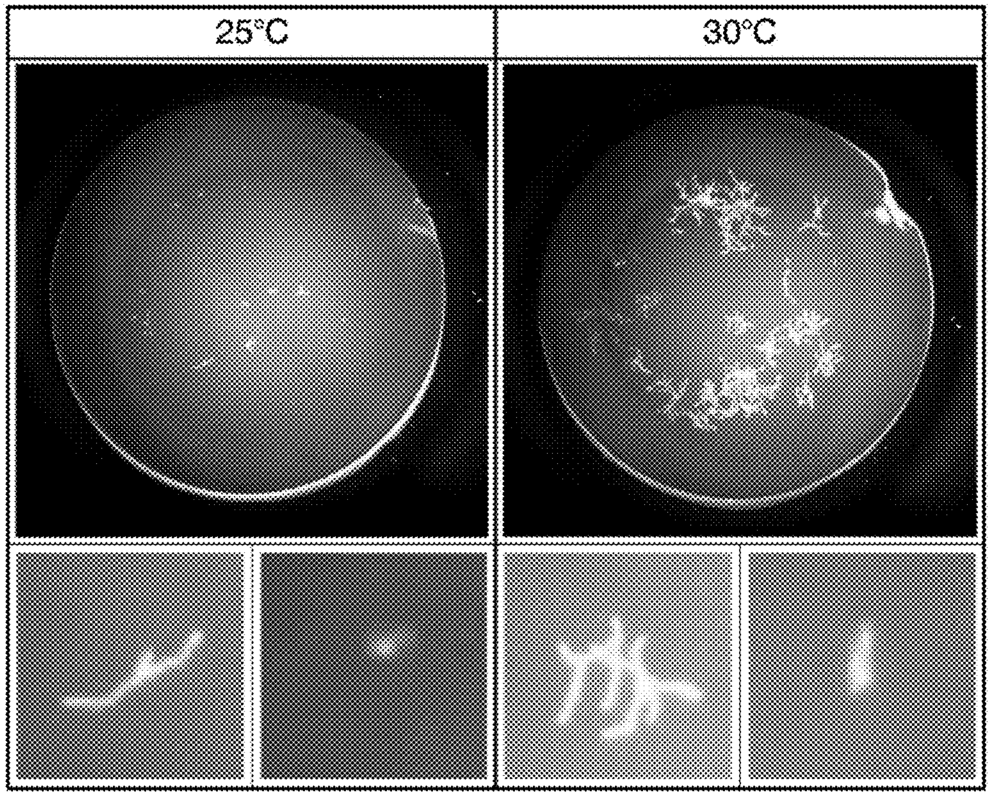
FIG. 9 shows fluorescence images of the membrane filters cultured on a PS25 plate medium at 25° C. (left) and 30° C. (right) after filtering a beverage inoculated with heat-resistant molds in Reference Example 1.
Figure 10:
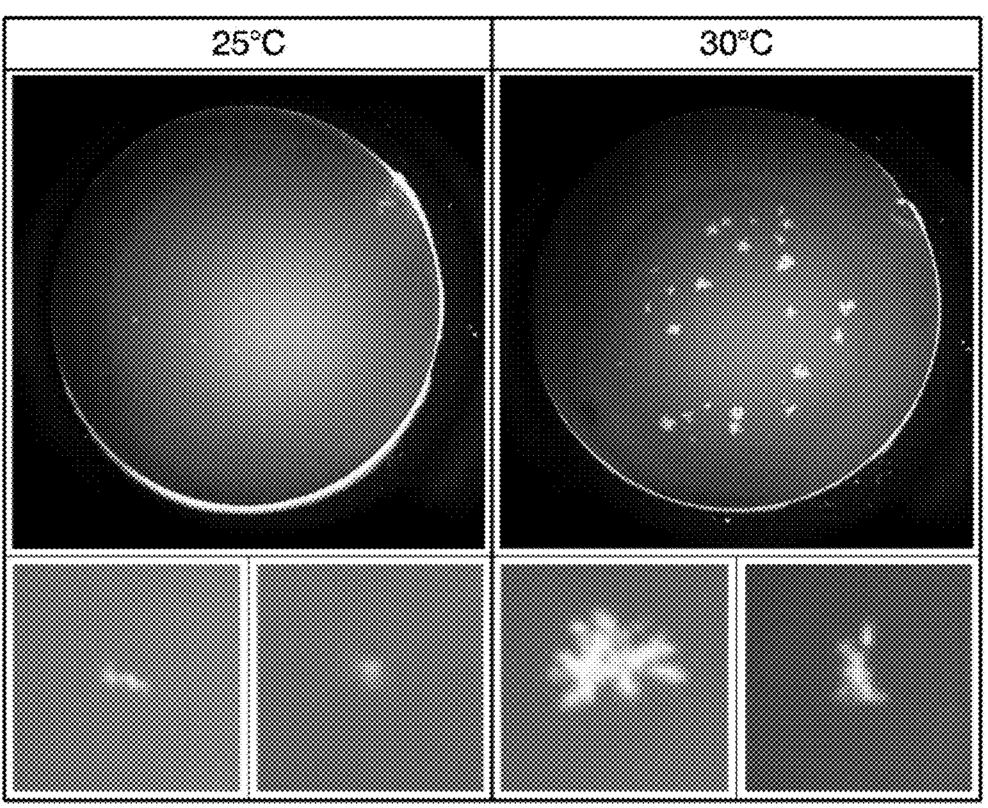
FIG. 10 shows fluorescence images of the membrane filters cultured on a PDA plate medium at 25° C. (left) and 30° C. (right) after filtering a beverage inoculated with heat-resistant molds in Reference Example 1.

FIG. 9 shows fluorescence images of the membrane filters cultured on the PS25 plate medium, and FIG. 10 shows fluorescence images of the membrane filters cultured on the PDA agar medium. In FIGS. 9 and 10, the left figure is a fluorescence image of the membrane filter cultured at 25° C., and the right figure is a fluorescence image of the membrane filter cultured at 30° C. In the figures, the lower part is an enlarged image of the portion where the fluorescence signals were observed in the upper fluorescence image. The optimum temperature for the heat-resistant mold *B. fulva* is 25-35° C. Therefore, although many colonies of heat-resistant molds were confirmed in the fluorescent image when cultured at 30° C., almost no colonies of heat-resistant molds were observed in the fluorescent image when cultured at 25° C. and the fluorescence signals in this fluorescence image were estimated to be noise.

Example 1

Four types of heat-resistant molds (*B. fulva, A. fischeri, T. flavus*, and *H. avellanea*) were each added to 2 types of commercially available milky non-carbonated beverages in an amount of 20 cfu per membrane filter used for filtration, and the obtained beverages were used a heat-resistant mold-inoculated beverage. In addition, a milky non-carbonated beverage of the same type as the test beverage, which was confirmed to contain no viable bacteria, was used as a blank beverage.

<Generation of Trained Model for Detecting Microorganisms>

Fluorescence images of the membrane filters that filtered the heat-resistant mold-inoculated beverage and the blank beverage were obtained in the same manner as in Reference Example 1, except that the culture was performed on a PS25 plate medium at 30° C. Thirty-two membrane filters were prepared from the heat-resistant mold-inoculated beverages, and 20 membrane filters were prepared from the blank beverage, and fluorescence images of each membrane filter were obtained. Of the 32 acquired fluorescence images of the heat-resistant mold-inoculated beverages, 16 were used as learning data, and the remaining 16 were used as detection data for verification using a trained model detecting microorganisms equipped with an algorithm generated by deep learning. Similarly, of the 20 acquired fluorescence images of the blank beverage, 10 were used as learning data, and the remaining 10 were used as detection data.

In order to generate learning data, the membrane filter of the heat-resistant mold-inoculated beverage was re-attached to the plate medium after fluorescence photography, and continuously cultured at 30° C. for 12 to 24 hours to confirm the position of the microbial colonies that had grown sufficiently to be visually confirmed. The reliability of the learning data was improved by feeding back the positional data of visually confirmed microbial colonies to the fluorescence detection results and identifying the fluorescence signals derived from the microorganisms on the membrane filter. As a deep learning software, "ViDi (VisionPro Deep Learning)" (manufactured by Cognex) was used. As a learning tool, a Red tool, which detects defects in an image and performs quality determination, or a Blue tool, which detects and measures a specific object in an image, was used.

Using the trained model for detecting microorganisms generated by deep learning, fluorescence signals derived from heat-resistant mold in fluorescence images used as the detection data were detected by distinguishing them from the noise. A recovery rate (%) represented by the following formula was calculated from the number of heat-resistant molds detected. The recovery rate is preferably 50 to 120%, more preferably 60 to 120%, even more preferably 70 to 120%, in order to achieve sufficient sensitivity in the detection of harmful microorganisms.

[Recovery rate (%)]=[Number of harmful microorganisms detected using trained model for detecting microorganisms]/[Number of harmful microorganisms detected using culture method]×100

Figure 11:
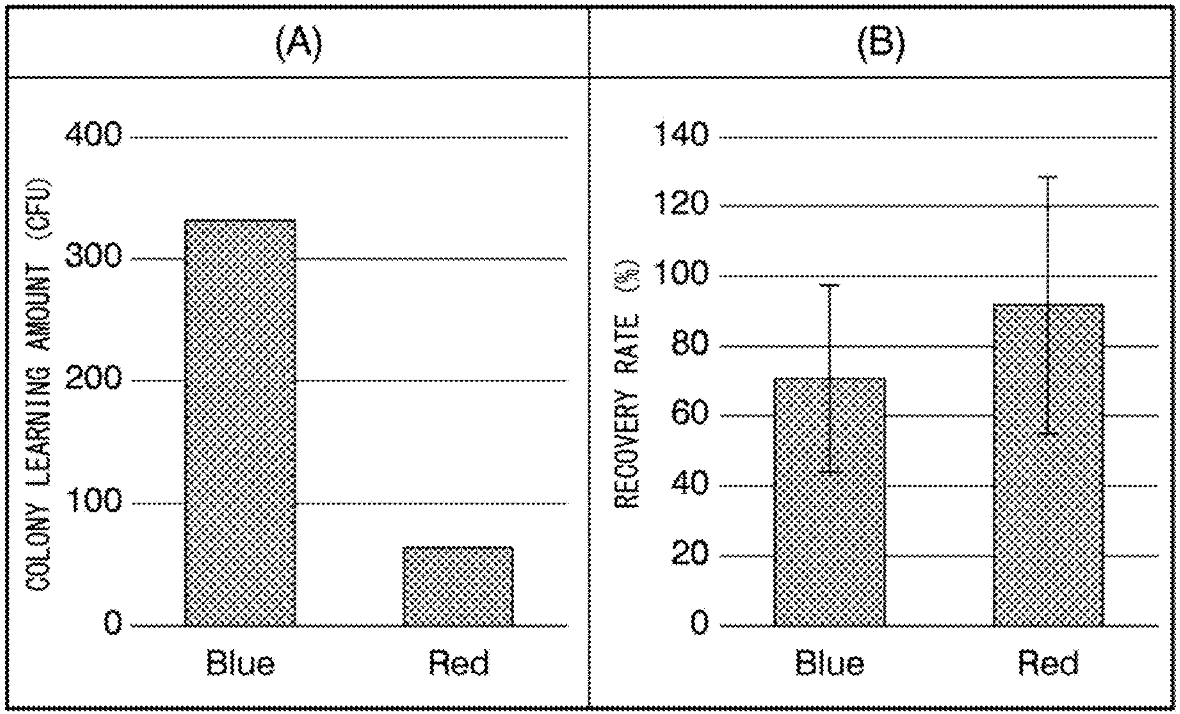
FIG. 11 is a diagram showing the result of detecting heat-resistant molds in a milky non-carbonated beverage using the trained model for detecting microorganisms generated using the Red tool and the Blue tool in Example 1.

FIG. 11(A) shows the measurement results of the colony number of heat-resistant molds (learning amount) used for learning when deep learning is performed using each learning tool, and FIG. 11(B) shows the recovery rate (%). As a result, when using the trained model for detecting microorganisms generated by deep learning using the Red tool, the recovery rate was nearly 100%, and this was better than using the trained model for detecting microorganisms generated by deep learning using the Blue tool. Further, the false positive rate shown by the following formula was 0% (0/10 sheets) for the trained models using either learning tool. In addition, in the following formula, "number of non-defective fluorescence images" is the number of fluorescence images of a membrane filter obtained by filtering a blank beverage. The false positive rate is preferably 0% in order to achieve sufficient accuracy in the detection of harmful microorganisms.

$$[\text{False positive rate}\,(\%)] = [\text{Number of fluorescence images determined to be false positive when using trained model for detecting microorganisms}]/[\text{Number of non-defective fluorescence images to be tested}] \times 100$$

Example 2

The influence of the trained model for detecting microorganisms in which the number of colonies for deep learning was generated on the detection accuracy of harmful microorganisms was investigated when detecting harmful microorganisms using a trained model for detecting microorganisms generated by deep learning using Red tools.

Four types of heat-resistant molds (*B. fulva, A. fischeri, T. flavus*, and *H. avellanea*) were each added to 5 types of commercially available milky non-carbonated beverages in an amount of 20 cfu per membrane filter used for filtration, and the obtained beverages were used a heat-resistant mold-inoculated beverage. In addition, a milky non-carbonated beverage of the same type as the test beverage, which was confirmed to contain no viable bacteria, was used as a blank beverage.

Fluorescence images of the membrane filters that filtered the heat-resistant mold-inoculated beverage and the blank beverage were obtained in the same manner as in Example 1 Forty membrane filters were prepared from the heat-resistant mold-inoculated beverages, and 50 membrane filters were prepared from the blank beverage, and fluorescence images of each membrane filter were obtained. Of the 40 acquired fluorescence images of the heat-resistant mold-inoculated beverages, 20 were used as learning data, and the remaining 20 were used as detection data for verification using a trained model detecting microorganisms equipped with an algorithm generated by deep learning. Similarly, of the 50 acquired fluorescence images of the blank beverage, 25 were used as learning data, and the remaining 25 were used as detection data.

Figure 12:
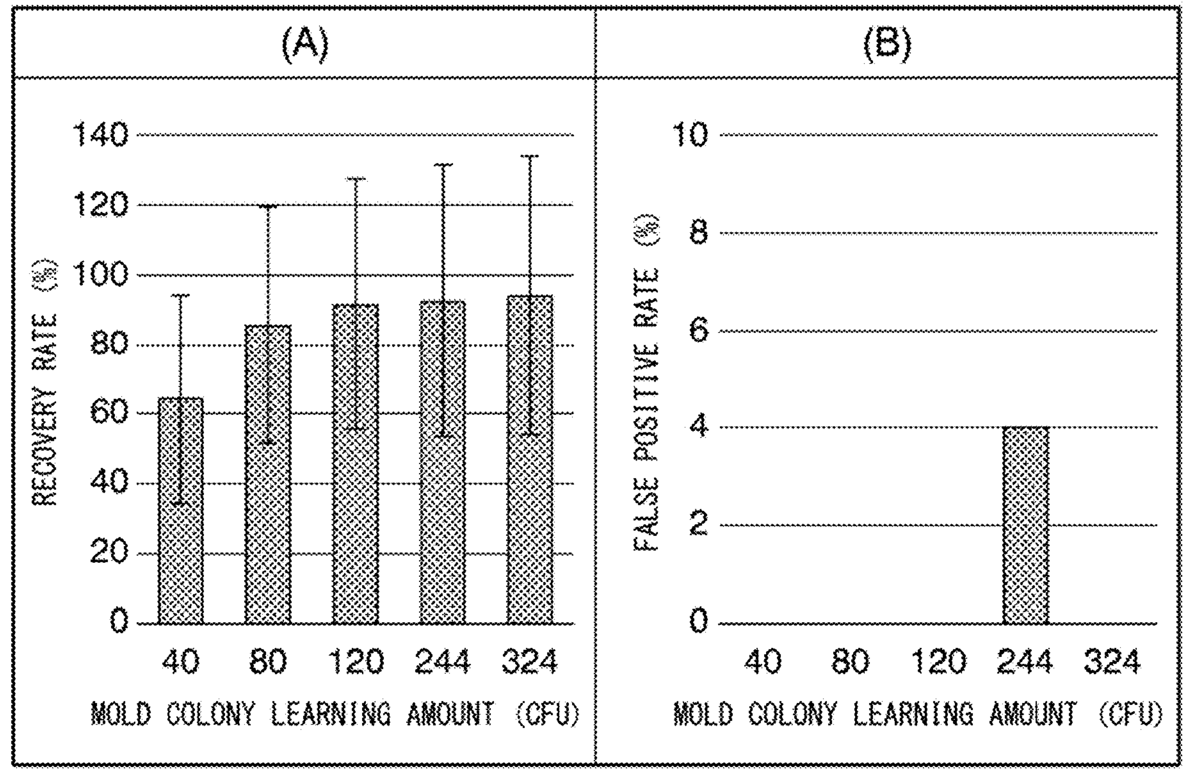
FIG. 12 is a diagram showing the measurement results of the recovery rate (%) (A) and the false positive rate (%) (B) when heat-resistant molds were detected in a milky non-carbonated beverage in Example 2 using a trained model for detecting microorganisms generated with a colony learning amount of 40, 80, 120, 244, or 324 cfu.

A trained model for microorganism detection was generated from the acquired learning data, and heat-resistant molds were detected in the fluorescent image used as detection data using the trained model for detecting microorganisms in the same manner as in Example 1 except that the Red tool was used as the learning tool. The recovery rate (%) and false positive rate (%) were measured when the colony learning amount was 40, 80, 120, 244, or 324 cfu. The measurement results are shown in FIG. 12. It was found that the colony learning amount is preferably around 300 because the recovery rate is high and the false positive rate is small.

Using a trained model for detecting microorganisms that was generated with a colony learning amount of 324 cfu, heat-resistant molds were detected in a commercially available lactic acid beverage containing a large amount of dead lactic acid bacteria. Two types of heat-resistant fungi (*B. fulva, A. fischeri*) were each added to a commercially available lactic acid bacteria beverage in an amount of 20 cfu per membrane filter used for filtration, and the obtained beverages were used as a heat-resistant mold-inoculated beverage. In addition, a lactic acid bacteria beverage of the same type as the above lactic acid bacteria beverage, which was confirmed to contain no viable bacteria, was used as a blank beverage.

Figure 13:
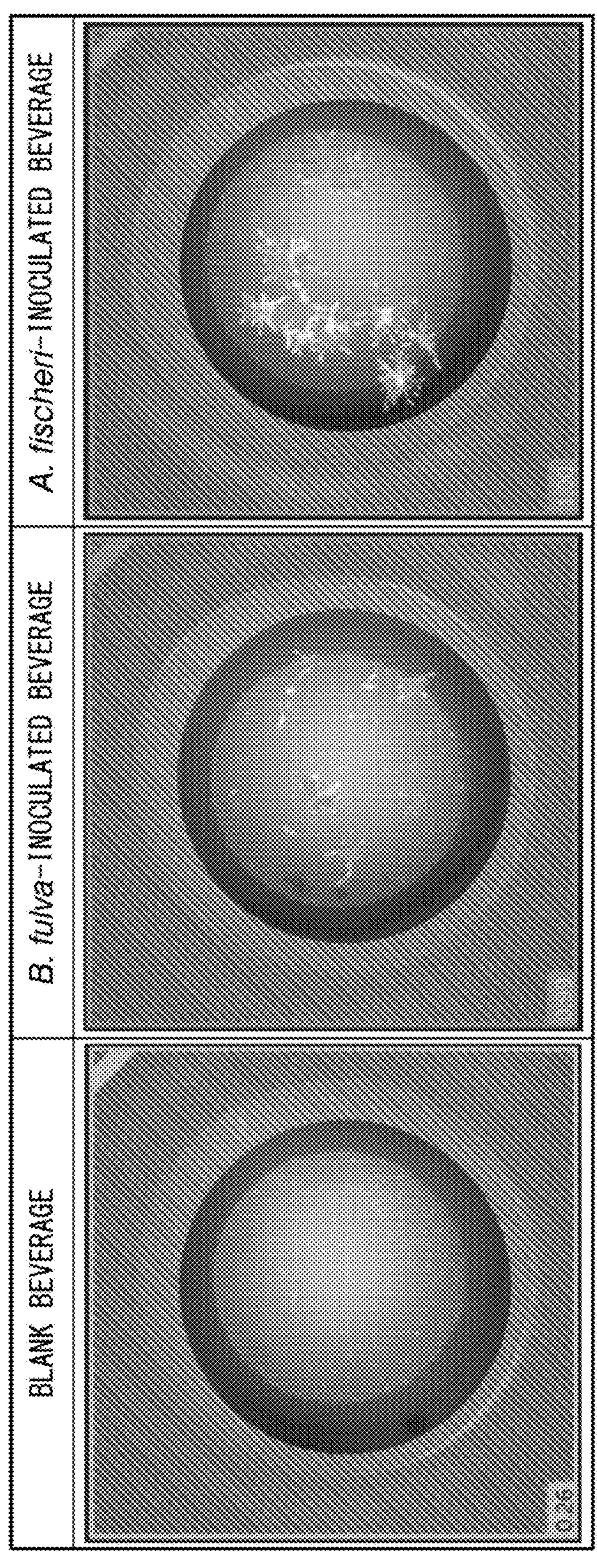
FIG. 13 shows fluorescence images of a blank lactic acid bacteria beverage and a lactic acid bacteria beverage inoculated with heat-resistant molds in Example 2.

Among the fluorescence signals in each fluorescence image, fluorescence signals derived from heat-resistant molds were detected using a trained model for detecting microorganisms. The results are shown in FIG. 13. Although the fluorescence image of the blank beverage contained a lot of noise due to autofluorescence emitted from the dead lactic acid bacteria, colonies could be specifically detected in the fluorescence images of the beverages inoculated with heat-resistant molds (*B. fulva, A. fischeri*). For each fluorescence image, the determination score was calculated using the criteria of 0 for fluorescence images in which heat-resistant mold was not detected and 1.0 for fluorescence images in which heat-resistant mold was detected. The score for the blank beverage was 0.26, the score for the heat-resistant mold-inoculated beverage inoculated with *B. fulva* was 0.99, and the score for the heat-resistant mold-inoculated beverage inoculated with *A. fischeri* was 1.00. The larger the difference between the determination score of the blank beverage and the determination score of the heat-resistant mold-inoculated beverage containing heat-resistant molds, the higher the heat-resistant mold detection accuracy of the used trained model for detecting microorganisms. In this example, since the difference in the pass/fail judgment score between the fluorescence image of the blank beverage and the fluorescence image of the mold-inoculated beverage was large, even if there were many noise components in the test beverage, it was possible to clearly determine the presence or absence of harmful microorganisms by using a trained model for detecting microorganisms generated by deep learning.

Example 3

During deep learning, the detection accuracy of harmful microorganisms was compared between a trained model for detecting microorganisms generated by performing non-defective product learning and a trained model for detecting microorganisms generated without performing non-defective product learning.

Four types of heat-resistant molds (*B. fulva, A. fischeri, T. flavus*, and *H. avellanea*) were each added to 5 types of commercially available milky non-carbonated beverages in an amount of 20 cfu per membrane filter used for filtration, and the obtained beverages were used a heat-resistant mold-inoculated beverage. In addition, a milky non-carbonated beverage of the same type as the test beverage, which was confirmed to contain no viable bacteria, was used as a blank beverage.

Fluorescence images of the membrane filters that filtered the heat-resistant mold-inoculated beverage and the blank beverage were obtained in the same manner as in Example 1 Forty membrane filters were prepared from the heat-resistant mold-inoculated beverages, and 50 membrane filters were prepared from the blank beverage, and fluorescence images of each membrane filter were obtained. Of the 40 acquired fluorescence images of the heat-resistant mold-inoculated beverages, 20 were used as learning data, and the remaining 20 were used as detection data for verification using a trained model detecting microorganisms equipped with an algorithm generated by deep learning. In the case of with non-defective product learning, of the 50 acquired fluorescence images of the blank beverage, 25 were used as learning data, and the remaining 25 were used as detection data. In the case of without non-defective product learning, of the 50 acquired fluorescent images of the blank beverage, 25 were used as detection data and not used as learning data.

Figure 14:
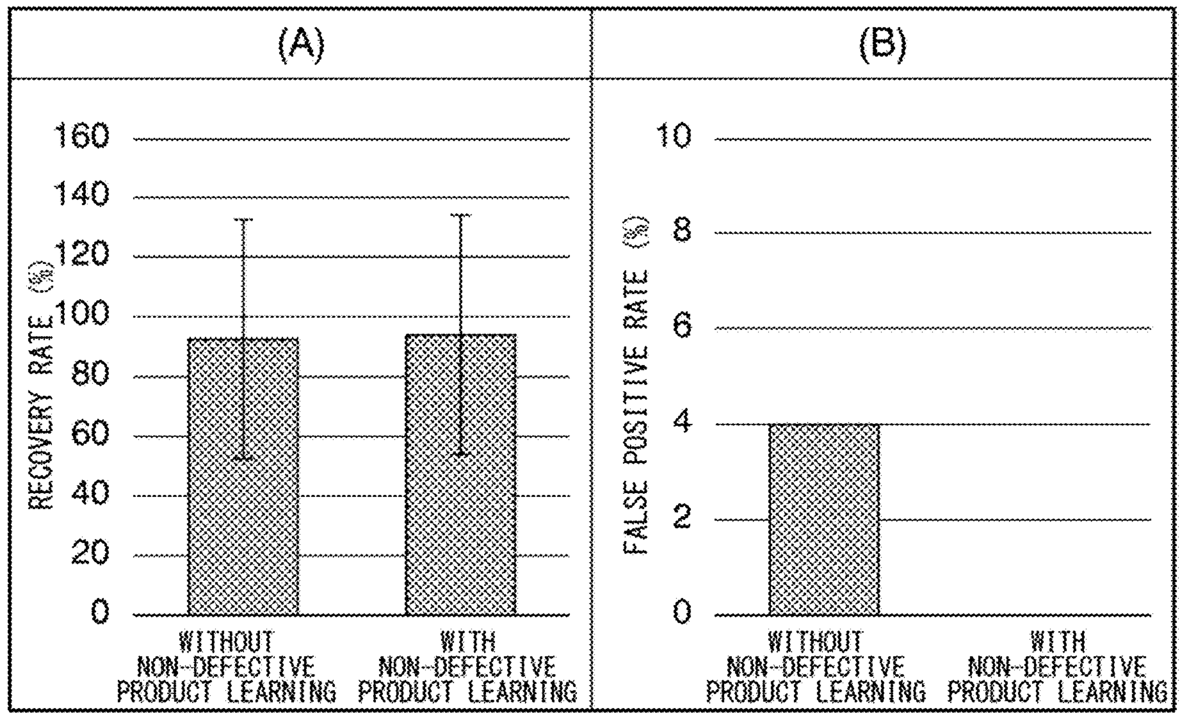
FIG. 14 is a diagram showing the measurement results of the recovery rate (%) (A) and the false positive rate (%) (B) when heat-resistant molds were detected in a milky non-carbonated beverage in Example 3 using a trained model for detecting microorganisms generated by non-defective product learning or a trained model for detecting microorganisms generated without non-defective product learning.

A trained model for microorganism detection was generated from the acquired learning data, and heat-resistant molds were detected in the fluorescent image used as detection data using the trained model for detecting microorganisms in the same manner as in Example 2. Recovery rate (%) and false positive rate (%) when using a trained model for microorganism detection generated with non-defective product learning and when using a trained model for microorganism detection generated without non-defective product learning were measured. The measurement results are shown in FIG. 14. Although whether or not a non-defective product learning is performed when generating a trained model for detecting microorganisms showed a small effect on the recovery rate (FIG. 14(A)), the trained model for detecting microorganisms generated with non-defective product learning showed a lower false positive rate and very good detection accuracy for heat-resistant molds.

Example 4

Using the Red tool as a learning tool, the colony learning amount was set to 300, and the performance of a trained model for detecting microorganisms generated by performing deep learning with non-defective product learning was compared with that of a microorganism rapid detection system kit (product name "Milliflex Rapid", manufactured by Merck).

Three types of heat-resistant molds (*B. fulva, A. fischeri* and *T. flavus*) were each added to 5 types of commercially available milky beverages in an amount of 20 cfu per membrane filter used for filtration, and the obtained beverages were used a heat-resistant mold-inoculated beverage. In addition, a milky beverage of the same type as the test beverage, which was confirmed to contain no viable bacteria, was used as a blank beverage.

A trained model for detecting microorganisms was prepared in the same manner as in Example 3, except that the colony learning amount was set to 300 and deep learning was performed with non-defective product learning. Heat-resistant molds were detected from the fluorescence image of each heat-resistant mold-inoculated beverage in the same manner as in Example 3, except that the prepared trained model for detecting microorganisms was used, and the recovery rate (%) was measured. In addition, as a comparison, heat-resistant molds were detected in the same manner using a commercially available microorganism rapid detection system kit "Milliflex Rapid", and the recovery rate (%) was measured. The recovery rate (%) of microorganisms detected using Milliflex Rapid is hereinafter referred to as "MFX recovery rate (%)".

Figure 15:
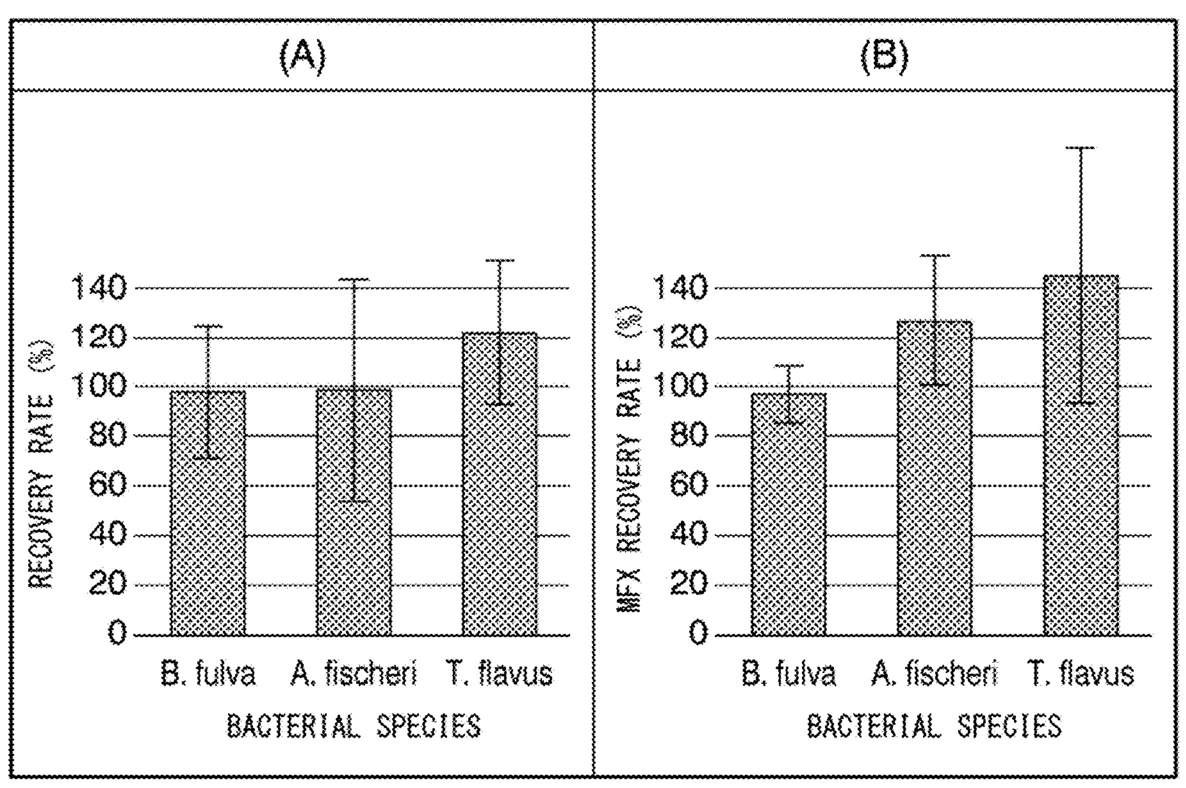
FIG. 15 shows the measurement results of the recovery rate (%) of each heat-resistant mold (average value of 5 types of milky beverages) when detected using the trained model for detecting microorganisms prepared in the Example (A) and when detected using a commercially available rapid microorganism detection system kit (B) in Example 4.

FIG. 15 shows the measurement results of the recovery rate (%) of each heat-resistant mold (average value of 5 varieties of milky beverages). FIG. 15(A) shows the recovery rate (%) detected using the trained model for detecting microorganisms generated in this Example, and FIG. 15(B) shows the MEX recovery rate detected using "Milliflex Rapid" (%) results. The recovery rate when using the trained model for detecting microorganisms generated in this Example exceeded 70% for all heat-resistant molds, and was comparable to the rapid detection system kit for microorganisms on the market and was good.

Example 5

Using the Red tool as a learning tool, the performance of a trained model for detecting microorganisms generated by performing deep learning was compared with that of the microorganism rapid detection system kit (product name "Milliflex Rapid", manufactured by Merck).

Five types of heat-resistant molds (*S. cerevisiae, Z. fermentati, C. krusei, T. delbrueckii*, and *Z. bailii*) were each added to 3 types of commercially available milky beverages in an amount of 30 cfu per membrane filter used for filtration, and the obtained beverages were used a yeast-inoculated beverage. In addition, a milky beverage of the same type as the test beverage, which was confirmed to contain no viable bacteria, was used as a blank beverage.

<Preparation of Trained Model for Detecting Microorganisms>

Fluorescent images of the membrane filters that filtered the yeast-inoculated beverage and the blank beverage were obtained in the same manner as in Example 1, except that the culture was carried out in a PS25 plate medium at 30° C. for 24 hours, the CFDA staining was carried out by incubating at 30° C. for 10 minutes, and the number of colonies learned was 900. Forty-five membrane filters were prepared from each of the yeast-inoculated beverage and the blank beverage, and fluorescence images of each membrane filter were obtained. Of the 45 fluorescence images acquired for each beverage, 30 were used as learning data, and the remaining 15 were used as detection data for verification using a trained model for detecting microorganisms equipped with an algorithm generated by deep learning.

In order to generate learning data, the membrane filter of the yeast-inoculated beverage was re-attached to the plate medium after fluorescence photography, and continuously cultured at 30° C. for 12 to 24 hours to confirm the position of the microbial colonies that had grown sufficiently to be visually confirmed. The reliability of the learning data was improved by feeding back the positional data of visually confirmed microbial colonies to the fluorescence detection results and identifying the fluorescence signals derived from the microorganisms on the membrane filter.

Yeasts were detected from the fluorescence image of each yeast-inoculated beverage in the same manner as in Example 3, except that the prepared trained model for detecting microorganisms was used, and the recovery rate (%) was measured. In addition, as a comparison, yeasts were detected in the same manner using a commercially available microorganism rapid detection system kit "Milliflex Rapid", and the MFX recovery rate (%) was measured.

Figure 16:
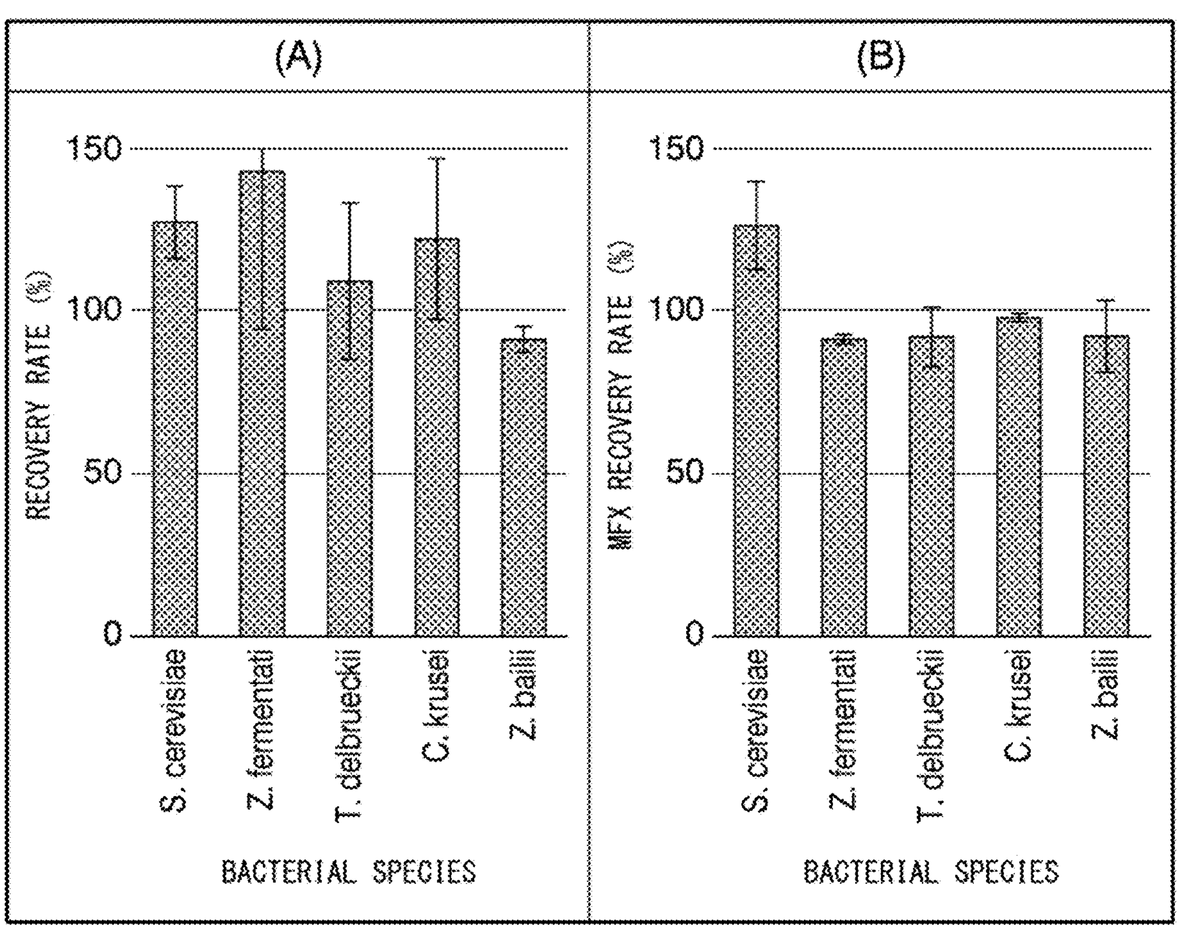
FIG. 16 is a diagram showing the measurement results of the recovery rate (%) of each yeast (average value of 3 types of milky carbonated lactic acid beverages) when detected using the trained model for detecting microorganisms prepared in the Example (A) and when detected using a commercially available rapid microorganism detection system kit (B) in Example 5.

FIG. 16 shows the measurement results of the recovery rate (%) of each yeast (average value of 3 varieties of milky carbonated beverages). FIG. 16(A) shows the recovery rate (%) detected using the trained model for detecting microorganisms generated in this Example, and FIG. 16(B) shows the MEX recovery rate detected using "Milliflex Rapid" (%) results. The recovery rate when using the trained model for detecting microorganisms generated in this Example exceeded 90% for all yeasts, and was comparable to the rapid detection system kit for microorganisms on the market and was good.

Although one embodiment of the present invention has been described in detail above with reference to the drawings, the specific configuration is not limited to the above, and various design changes, etc., can be made without departing from the scope of the present invention.

For example, the learning data generation unit 131 may display a fluorescence image of the same membrane filter with different incubation time, and allow the user to mark the fluorescence image with a long incubation time. In this case, the learning data generation unit 131 may display the marking at the same position as the marked position in the fluorescence image with the short incubation time, or may use the position as the microorganism position information. Here, the fluorescence image with a short incubation time is used as learning data. Further, the learning data generation unit 131 identifies, based on the additional information, that the fluorescence image is obtained from the same membrane filter although the culture times are different.

In this way, the learning device 1 allows the user to identify the microorganism position information using a fluorescence image with a long culture time that allows the presence or absence of harmful microorganisms to be determined with the human eye, or to be determined easily. As a result, the learning device 1 can accurately identify the position of microorganisms even on a fluorescence image in which the presence or absence of harmful microorganisms cannot be determined with the human eye, or is difficult to determine, and the culture time is short. In other words, regarding the microorganisms in the fluorescent images used for learning, by observing the future state (longer time, after culture) of microorganisms in a fluorescence image, microorganism location information can be identified.

A part of the learning device 1 or the inspection device 2 in the above-described embodiment may be achieved by a computer. In that case, a program for achieving this control function may be recorded in a computer-readable recording medium, and the program recorded in this recording medium may be read into a computer system and executed. The "computer system" here refers to a computer system built in the learning device 1 or the inspection device 2, and includes hardware such as an OS and peripheral devices. In addition, the term "computer-readable recording medium" refers to portable media such as flexible discs, magneto-optical discs, ROMs and CD-ROMs, and storage devices such as hard discs incorporated in computer systems. Furthermore, "computer-readable recording medium" may also include a medium that dynamically stores a program for a short period of time, such as a communication line for transmitting a program via a network such as the Internet or a communication line such as a telephone line, and a medium that holds a program for a certain period of time, such as a volatile memory inside a computer system that serves as a server or client in the former case. Further, the above-described program may be one for achieving some of the above-described functions, or may also be one that can achieve the above-described functions in combination with a program already recorded in the computer system.

Furthermore, some or all of the learning device 1 and the inspection device 2 in the above-described embodiment may be achieved as an integrated circuit such as LSI (Large-Scale Integration) or the like. Each functional block of the learning device 1 and the inspection device 2 may be individually achieved as a processor, and may also be achieved as a processor by integrating some or all of them. Further, the method of circuit integration is not limited to LSI, and it may be achieved by a dedicated circuit or a general-purpose processor. In addition, in a case where an integrated circuit technology emerges to replace LSI due to advances in semiconductor technology, an integrated circuit based on this technology can be used.

Although one embodiment of the present invention has been described above in detail with reference to the drawings, the specific configuration is not limited to the above-described embodiment, and various design changes, etc., can be made without departing from the scope of the present invention.

[Reference Signs List]

| | | |
|---|---|---|
| 1: Learning device | I1: Input/output unit | M1: Memory unit |
| P1: Processing unit | 111: Data acquisition unit | 112: Input/output unit |
| 121: Data Storage unit | 122: Learning data storage unit | |
| 123: Learning result storage unit | 131: Learning data generation unit | |
| 132: Preprocessing unit | 133: Learning unit | 134: Display control unit |
| 2: Inspection device | I2: Input/output unit | M2: Memory unit |
| P2: Processing unit | 211: Image acquisition unit | 212: Input unit |
| 213: Display unit | 221: Terminal data storage unit | 222: Setting storage unit |
| 223: Trained model storage unit | 231: Setting unit | 232: Inspection unit |
| 233: Display control unit | | |

The invention claimed is:

1. A method for detecting microorganisms in a liquid, comprising:
- a filtering step of filtering a liquid with a membrane filter;
- a culturing step of attaching the membrane filter after the filtering step to a surface of a plate medium and culturing for a predetermined period of time;
- a fluorescent staining step of fluorescently staining microorganisms on the membrane filter peeled off from the plate medium after the culturing step;
- an imaging step of imaging fluorescence images of the membrane filter after the fluorescent staining step;
- a learning data generation step of inputting, for each of the plurality of the fluorescence images, microorganism position information indicating the microorganism positions on the fluorescence images to generate, as learning data, the fluorescence images and the microorganism position information;
- a learning step of generating a trained model by performing machine learning based on the learning data; and
- an inspection step of determining the presence or absence of microorganisms using the trained model to identify whether a fluorescent signal of each pixel in inspection fluorescence images input as an inspection target is a fluorescent signal derived from the microorganisms or noise.

2. The method for detecting microorganisms according to claim 1, further comprising a pre-step of removing an edge portion of the membrane filter from the fluorescence images, wherein
- in the learning step, machine learning is performed based on the fluorescence images from which the edge portion of the membrane filter has been removed and the microorganism position information.

3. The method for detecting microorganisms according to claim 1, wherein in the imaging step, the fluorescence images are imaged by irradiating excitation light of a fluorescent staining agent used for the fluorescence staining.

4. The method for detecting microorganisms according to claim 1, wherein
- the plate medium contains glucose, peptone and potato extract, and
- the peptone concentration is 2 to 5 g/L.

5. The method for detecting microorganisms according to claim 1, wherein the plate medium consists only of glucose, peptone, potato extract, and agar.

6. The method for detecting microorganisms according to claim 1, wherein the liquid is a beverage.

7. A learning device comprising a processor configured to read, as learning data, fluorescence images obtained by imaging a membrane filter cultured with microorganisms collected from a liquid and fluorescently stained with a fluorescent staining agent for microorganisms and microorganism position information indicating the microorganism positions on the fluorescence images, the learning data obtained following a predetermined period of time after the microorganisms are cultured, and generate a trained model configured to identify whether a fluorescent signal of each pixel in inspection fluorescence images input as an inspection target is a fluorescent signal derived from the microorganisms or noise by performing machine learning based on the learning data.

8. An inspection device comprising a processor configured to determine the presence or absence of microorganisms by identifying whether a fluorescent signal of each pixel in inspection fluorescence images input as an inspection target is a fluorescent signal derived from the microorganisms or noise using a trained model generated by performing machine learning based on fluorescence images obtained by imaging a membrane filter cultured with microorganisms collected from a liquid and fluorescently stained with a fluorescent staining agent for microorganisms and microorganism position information indicating the microorganism positions on the fluorescence images, wherein the fluorescent signals are identified following a predetermined period of time after the microorganisms are cultured.

* * * * *